US010890578B2

(12) United States Patent
Abbott et al.

(10) Patent No.: US 10,890,578 B2
(45) Date of Patent: Jan. 12, 2021

(54) USING LIQUID CRYSTAL TO DETECT ENDOTOXIN IN THE PRESENCE OF ONE OR MORE POTENTIAL MASKING AGENTS

(71) Applicant: Wisconsin Alumni Research Foundation, Madison, WI (US)

(72) Inventors: Nicholas Abbott, Madison, WI (US); Abhijit Dan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 48 days.

(21) Appl. No.: 16/060,471

(22) PCT Filed: Dec. 9, 2016

(86) PCT No.: PCT/US2016/065716
§ 371 (c)(1),
(2) Date: Jun. 8, 2018

(87) PCT Pub. No.: WO2017/100503
PCT Pub. Date: Jun. 15, 2017

(65) Prior Publication Data
US 2019/0257821 A1    Aug. 22, 2019

Related U.S. Application Data

(60) Provisional application No. 62/265,498, filed on Dec. 10, 2015.

(51) Int. Cl.
*G01N 33/52*    (2006.01)
*G01N 33/92*    (2006.01)
(Continued)

(52) U.S. Cl.
CPC .......... *G01N 33/521* (2013.01); *G01N 15/14* (2013.01); *G01N 27/22* (2013.01); *G01N 33/52* (2013.01); *G01N 33/92* (2013.01)

(58) Field of Classification Search
CPC ...... G01N 15/14; G01N 27/22; G01N 33/521; G01N 33/92
See application file for complete search history.

(56) References Cited

U.S. PATENT DOCUMENTS 7,135,143 B2 * 11/2006 Abbott ................ B82Y 15/00
                                                          422/82.05
7,724,319 B2 *  5/2010 Abbott ................ C09K 19/00
                                                             349/199
(Continued)

FOREIGN PATENT DOCUMENTS

WO    2010/126774 A1    11/2010

OTHER PUBLICATIONS

European Patent Office as International Searching Authority; International Search Report and Written Opinion of the International Searching Authority for PCT/US2106/065716; dated Mar. 9, 2017; pp. 1-13.

(Continued)

*Primary Examiner* — Jennifer Wecker
(74) *Attorney, Agent, or Firm* — Boyle Fredrickson S.C.

(57) ABSTRACT

Devices and methods for using changes in the configuration of micrometer sized dispersed liquid crystal domains to detect or quantify analytes in a test sample, including endotoxin lipopolysaccharide (LPS), are disclosed. The test sample includes one or more potential masking agents, such as a non-ionic surfactant, a chelating agent, a divalent cation, a protein, or a nucleic acid, and may also include a buffer. The dispersed liquid crystal microdomains are exposed to the test sample, and any changes in the configuration in the liquid crystal microdomains, such as from the bipolar to radial configuration, are detected. Such changes in configuration signal the presence of analyte in the test sample, and the proportion of liquid crystal microdomains exhibiting the change in configuration is correlated with the quantity of analyte in the test sample.

20 Claims, 16 Drawing Sheets

(51) Int. Cl.
*G01N 15/14* (2006.01)
*G01N 27/22* (2006.01)

(56) References Cited

U.S. PATENT DOCUMENTS

| | | | | |
|---|---|---|---|---|
| 2007/0004046 A1* | 1/2007 | Abbott | ................... | B82Y 15/00 |
| | | | | 436/104 |
| 2007/0042505 A1* | 2/2007 | Israel | ..................... | B82Y 30/00 |
| | | | | 436/518 |
| 2011/0007261 A1* | 1/2011 | Abbott | ................... | G01N 21/21 |
| | | | | 349/199 |
| 2013/0157379 A1* | 6/2013 | Nazareth | ................ | G01N 33/76 |
| | | | | 436/501 |

OTHER PUBLICATIONS

Vera Joanne Alino et al; "Liquid Crystal Droplets as a Hosting and Sensing Platform for Developing Immunoassays"; Langmuir, vol. 27, No. 19; Oct. 4, 2011; pp. 11784-11789.

Tanmay Bera et al; "Protein-Induced Configuration Transitions of Polyelectrolyte-Modified Liquid Crystal Droplets", Journal of Physical Chemistry Part B: Condensed Matter, Materials, Surfaces, Interfaces and Biophysical, vol. 118, No. 18; May 8, 2014; pp. 4970-4975.

* cited by examiner

USING LIQUID CRYSTAL TO DETECT ENDOTOXIN IN THE PRESENCE OF ONE OR MORE POTENTIAL MASKING AGENTS

CROSS-REFERENCE TO RELATED APPLICATIONS

This application is the U.S. national phase entry of International Application No. PCT/US2016/065716, which claims the benefit of U.S. provisional Application No. 62/265,498 filed on Dec. 10, 2015. Each of these applications is incorporated by reference herein in its entirety.

STATEMENT REGARDING FEDERALLY SPONSORED RESEARCH OR DEVELOPMENT

This invention was made with government support under DMR1121288 and DMR0832760 awarded by the National Science Foundation, W911NF-10-1-0181 and W911NF-11-1-0251 awarded by the Army/ARO and CA108467 awarded by the National Institutes of Health. The government has certain rights in the invention.

FIELD

This disclosure relates generally to methods of analyte detection using liquid crystals. In particular, the disclosure is directed to systems and methods utilizing micrometer-sized domains of liquid crystal to detect and quantify analytes such as endotoxin lipopolysaccharide (LPS) in a test sample that includes one or more potential masking agents that are known to affect the accuracy of other assays used for detecting and/or quantifying such analytes.

BACKGROUND

Detecting and quantifying endotoxin lipopolysaccharide (LPS) is critically important in a wide range of health-related contexts, including human healthcare, clinical and basic medical research, pharmaceutical manufacturing, occupational and public health, and food and water purity testing. Currently, the most commonly used methods for endotoxin detection and quantification are based on the *Limulus* Amoebocyte Lysate-related gelation reaction or chromogenic response as modified from the original *Limulus* Amoebocyte Lysate Assay (LAL Assay), which was first disclosed in 1960s.

The *Limulus* Amoebocyte is the only circulating cell found in the blood of *Limulus polyphemus*, the horseshoe crab. When a horseshoe crab acquires a Gram-negative bacterial infection, the *Limulus* Amoebocyte Lysate enzyme interacts with the Lipid A portion of the LPS produced and triggers extracellular coagulation. This reaction is the basis of a number of assay methods used for detecting and quantifying endotoxin in aqueous specimens (e.g., kinetic turbidimetric LAL assay, kinetic chromogenic LAL assay, Gel-Clot LAL, and End-Point LAL), and endotoxin detection limits using these assays can be as low as the pg/mL range.

The current LAL-based assays have a number of disadvantages. For example, LPS isolated from different species of bacteria do not activate LAL equally. In addition, certain substances interfere with LAL's ability to react with endotoxin. Furthermore, since the lysate is a crude and variable mixture, not a single purified enzyme, the enzyme activity needs to be standardized using a complex and expensive procedure for every batch of LAL extracted. The reagents for LAL assays are also derived from animals, and the reagents need to be stored under controlled conditions, such as controlled temperature. In general, the complexity of the assays requires the use of skilled technicians.

It has long been known that the presence of certain metal ions may activate or inhibit the LAL chromogenic reaction. For example, the addition of $Mg^{2+}$ ion activates the LAL chromogenic reaction, while $Ca^{2+}$ ion in concentrations above 5 mM inhibits the reaction. The presence of as little as 0.3 mM $Zn^{2+}$ ion strongly inhibits the reaction, while inhibition by $Zn^{2+}$ is partly suppressed by the addition of 160 mM $Mg^{2+}$ (see Guyomard, S. et al., Ann. Inst. Patsteur/Microbiol. 1985, 136B, 49-55).

It has further been reported that the addition of divalent cations results in false negatives when performing the LAL assay, putting into question the accuracy of endotoxin values measured in DNA purified using salt precipitation techniques (see Clarence M. Ongkudon, C. M. and Danquah, M. K., Analytical Chemistry 2011, 83, 391-397). Furthermore, $Ca^{2+}$ has been shown to be inhibitory to endotoxin inactivation with heated extracts of LAL, with partial inhibition at 0.001 M $Ca^{2+}$ and complete inhibition at 0.02 M $Ca^{2+}$. Other divalent cations, including $Mg^{2+}$, $Ba^{2+}$, $Mn^{2+}$, and $Cu^{2+}$, have also been found to inhibit the inactivation of endotoxin (see Nachum, R. et al., Journal of Invertebrate Pathology 1978, 32(1), 51-58; Bamba, T. et al., Journal of Pharmaceutical Science and Technology 1996, 50(2), 129-135).

In addition, recent published reports have identified certain combinations of surfactants and buffers commonly used to formulate therapeutic proteins and other biological reagents that can mask the response to endotoxin of the FDA-approved LAL assay. This phenomenon is known as low endotoxin recovery (LER). For example, the LAL assay is unable to accurately report a known amount of purified LPS from a solution in the presence of Tween 20/citrate. LER is time-dependent, and surfactant/buffer conditions can lead to very fast masking kinetics—the complete masking of LPS often requires less than an hour, after which the endotoxin cannot be recovered. Nucleic acids or proteins present in therapeutic compositions could also potentially interfere with the LAL assay by masking any endotoxin present, rendering it undetectable.

These and other issues with the LAL assay are significant problems for both the biopharmaceutical industry and assay suppliers. The limitations of current assays for endotoxin LPS demonstrate a continuing need for a simple yet accurate assay for reporting and quantifying LPS in aqueous samples, particularly in the presence of divalent cations, non-ionic surfactants, chelating agents, buffers, proteins, and/or nucleic acids, each of which is known to affect the accuracy of the standard LAL assay.

In U.S. Pat. No. 9,080,973 issued on Jul. 14, 2015, U.S. Pat. No. 9,341,571 issued on May 17, 2016, and U.S. Patent Publication No. 2016/0223573 published on Aug. 4, 2016, each of which is incorporated by reference herein in its entirety and for all purposes, a liquid crystal-based assay for quantifying endotoxin LPS is disclosed. Specifically, liquid crystal (LC) droplets dispersed in an aqueous solution were shown to signal the presence of endotoxin LPS with a readily detectable change in configuration from the bipolar (two point defects) to the radial (one point defect) configuration. The percentage of droplets that exhibit the radial configuration was correlated with both the density of the LC droplets within the aqueous solution and the concentration of endotoxin LPS in the solution. Accordingly, the '973 and '571 patents and the '573 publication demonstrate the use of dispersed liquid crystal microdomains to accurately quantify endotoxin LPS in a sample of interest.

However, the '973 and '571 patents and the '573 publication did not demonstrate that the disclosed method would maintain its accuracy under conditions that are known to affect the accuracy of the LAL assay, such as in the presence of divalent cations, masking proteins or nucleic acids, masking surfactants, masking chelating agent or buffers. Indeed, given that these agents appear to affect the results of the LAL assay by directly interacting with the endotoxin that is targeted by the assay, the skilled artisan would expect that the accuracy of the LC-based assays disclosed in the '973 and '571 patents and the '573 publication would also be affected by the presence of such agents.

Accordingly, there remains need in the art for assays for detecting and quantifying endotoxin LPS at low limits of detection that are accurate under and unaffected by conditions that are known to affect the accuracy and consistency of the LAL assay, including in the presence of potential masking agents.

SUMMARY

Surprisingly, we have discovered that the previously disclosed method of observing configurational transitions in micrometer-sized droplets of liquid crystal dispersed in aqueous solution to quantify endotoxin LPS is not affected by the presence of bivalent cations, non-ionic surfactants, chelating agents, buffers, or nucleic acids. In addition, the inventors have developed a method for effectively eliminating the masking effect of proteins within the composition that is being assayed.

Accordingly, in a first aspect, the disclosure encompasses a liquid crystal-based system for detecting an analyte in a test sample. The system includes (a) a plurality of dispersed liquid crystal microdomains that are confined by an interface that generates one or more point defects in the liquid crystal microdomains, wherein the liquid crystal microdomains have a minor axis of between about 0.5 µm and about 200 µm; and (b) a test sample in contact with the liquid crystal microdomains that includes a potential masking agent. The potential masking agent may be a non-ionic surfactant, a chelating agent, a divalent cation, a protein, a nucleic acid, or any combination of these.

In some embodiments, the system further includes a detector capable of characterizing the orientational ordering of the liquid crystal within the microdomains.

In some embodiments, at least one of the liquid crystal microdomains has one point defect.

In some embodiments, the test sample further includes an analyte. In some embodiments, the concentration of the analyte in the test sample is less than 1 µM. In some embodiments, the analyte is endotoxin lipopolysaccharide (LPS) or the lipid A part of LPS.

In some embodiments, the detector is a light-based imaging device. In some embodiments, the detector includes a flow cytometer. In some embodiments, the detector detects the scattering of light from the liquid crystal microdomains.

In some embodiments, the potential masking agent is a non-ionic surfactant. In some such embodiments, the non-ionic surfactant is Sorbitan monolaurate, Sorbitan monopalmitate, Sorbitan monostearate, Sorbitan monooleate, Sorbitan trioleate, Polyoxyethylene (20) sorbitan monolaurate, Polyoxyethylene (20) sorbitan monopalmitate, Polyoxyethylene (20) sorbitan monostearate, Polyoxyethylene (20) sorbitan mono-oleate, Polyoxyethylene (20) sorbitan tristearate, Polyoxyethylene (20) sorbitan tri-oleate, Triton X-100, Triton X-114, Triton X-405, Brij 30, Brij35, Brij 56, Brij 58, Brij78, Monolaurin, Nonoxynol-9, Pluronic P-123, Pluronic F-127, Cocamide DEA, or Cocamide MEA. In some embodiments, the test sample further includes one or more buffers.

In some embodiments, the potential masking agent is a chelating agent. In some such embodiments, the chelating agent is citric acid or a salt thereof, ethylenediaminetetracaetic acid (EDTA) or a salt thereof, aminotris(methylenephosphonic acid) (ATMP) or a salt thereof, 1,2-bis(o-aminophenoxy)ethane-N,N,N',N'-tetraacetic acid (BAPTA) or a salt thereof, a bipyridine, diethylenetriamine (DETA), 1,4,7,10-tetraazacyclododecane-1,4,7,10-tetraacetic acid (DOTA) or a salt thereof, diethylenetriaminepentaacetic acid (DTPA) or a salt thereof, diethylenetriamine penta(methylene phosphonic acid) (DTMP) or a salt thereof, ethylenediamine-N,N'-disuccinic acid (EDDS) or a salt thereof, ethylenediamine tetra(methylene phosphonic acid) (EDTMP) or a salt thereof, ethylene glycol-bis(3-aminoethyl ether)-N,N,N',N'-tetraacetic acid (EGTA) or a salt thereof, 1-hydroxyethane 1,1-diphosphonic acid (HEDP) or a salt thereof, gluconic acid or a salt thereof, iminodiacetic acid (IDA) or a salt thereof, nitrilotriacetic acid (NTA) or a salt thereof, oxalic acid or a salt thereof, polyaspartic acid (PASA) or a salt thereof, or triethylenetetramine (TETA) or a salt thereof.

In some embodiments, the potential masking agent is a divalent cation. In some such embodiments, the divalent cation is $Mg^{2+}$, $Zn^{2+}$, $Ca^{2+}$, or $Cu^{2+}$. In some embodiments, the test sample further includes a second potential masking agent that is a nucleic acid. In some such embodiments, the nucleic acid is DNA or RNA. In some such embodiments, the DNA is extracted from a bacterial plasmid. In some embodiments, the nucleic acids are micro-nucleic acids or small interfering nucleic acids. In other embodiments, the nucleic acids are synthetic derivatives, including peptide nucleic acid, morpholino- and locked nucleic acid, as well as glycol nucleic acid and threose nucleic acid.

In some embodiments, the potential masking agent is a protein. In some such embodiments, the protein is a protein that has been partially or fully digested by a protease.

In some embodiments, the potential masking agent is a nucleic acid. In some such embodiments, the nucleic acid is DNA or RNA. In some such embodiments, the DNA is extracted from a bacterial plasmid. In some embodiments, the nucleic acids are micro-nucleic acids or small interfering nucleic acids. In other embodiments, the nucleic acids are synthetic derivatives, including peptide nucleic acid, morpholino- and locked nucleic acid, as well as glycol nucleic acid and threose nucleic acid. In some embodiments, the aqueous test sample further includes a second potential masking agent that is a divalent cation. In some such embodiments, the divalent cation is $Mg^{2+}$, $Zn^{2+}$, $Ca^{2+}$, or $Cu^{2+}$.

In some embodiments, the liquid crystal making up the dispersed liquid crystal microdomains is 4'-pentyl-4-cyanobiphenyl (5CB). In other embodiments, the liquid crystal is a nematic liquid crystal.

In some embodiments, the liquid crystal microdomains are liquid crystal droplets. In some such embodiments, the liquid crystal droplets have a minor axis of from about 1 µm to about 10 µm. In some embodiments, the liquid crystal droplets are prepared by vortexing of aqueous dispersions of liquid crystal. In some embodiments, the liquid crystal droplets are prepared by mechanical agitation of the liquid crystal in the presence of concentrations of surfactants that are below that which triggers the radial configuration of the liquid crystal droplets. In some embodiments, vortexing or sonication is used as a form of mechanical agitation.

In a second aspect, the disclosure encompasses a method for detecting an analyte in a test sample. The method includes the steps of (a) contacting one or more dispersed liquid crystal microdomains having one or more point defects with a test sample, wherein the test sample includes a potential masking agent selected from the group consisting of a non-ionic surfactant, a chelating agent, a divalent cation, a protein, a nucleic acid, and combinations thereof; and (b) determining the configuration of the liquid crystal within the liquid crystal microdomains. A change in the configuration of the liquid crystal within the liquid crystal microdomains after being contacted with the test sample indicates the presence of the analyte in the test sample.

In some embodiments, the liquid crystal microdomains have a minor axis of between about 0.5 μm and about 200 μm.

In some embodiments, the change in the configuration of the liquid crystal within the liquid crystal microdomains corresponds to a change in the number of point defects within the liquid crystal microdomains.

In some embodiments, the change in the configuration of the liquid crystal within the liquid crystal microdomains is a change from bipolar to radial configuration. In some such embodiments, the change from bipolar to radial configuration corresponds to a reduction in the number of point defects from two (bipolar) to one (radial).

In some embodiments, a plurality of dispersed liquid crystal microdomains are contacted with the test sample.

In some embodiments, the step of determining the configuration of the liquid crystal within the liquid crystal microdomains is performed by one or more of optical imaging, fluorescence imaging, optical imaging using polarized light, polarized light microscopy, bright field microscopy, fluorescence microscopy, light scattering measurement, flow cytometry, fluorescence flow cytometry, microelectrophoresis, dielectrophoresis, measurement of electrical capacitance, measurement of magnetic properties, measuring turbidity, detecting optical reflection, detecting transmittance of light, visual inspection, using a plate reader, using microwell plates, or using a cuvette in a detector.

In some embodiments, the test sample further includes an analyte. In some such embodiments, the concentration of the analyte in the test sample is less than 1 μM. In some embodiments, the analyte is endotoxin lipopolysaccharide (LPS) or the lipid A part of LPS.

In some embodiments, the potential masking agent is a non-ionic surfactant. In some such embodiments, the non-ionic surfactant is Sorbitan monolaurate, Sorbitan monopalmitate, Sorbitan monostearate, Sorbitan mono-oleate, Sorbitan trioleate, Polyoxyethylene (20) sorbitan monolaurate, Polyoxyethylene (20) sorbitan monopalmitate, Polyoxyethylene (20) sorbitan monostearate, Polyoxyethylene (20) sorbitan mono-oleate, Polyoxyethylene (20) sorbitan tristearate, Polyoxyethylene (20) sorbitan tri-oleate, Triton X-100, Triton X-114, Triton X-405, Brij 30, Brij35, Brij 56, Brij 58, Brij78, Monolaurin, Nonoxynol-9, Pluronic P-123, Pluronic F-127, Cocamide DEA, or Cocamide MEA. In some embodiments, the test sample further includes one or more buffers. In some embodiments, the one or more buffers include one or more buffering salts. In some embodiments, the buffering salts include citrate or phosphate ions.

In some embodiments, the potential masking agent is a chelating agent. In some such embodiments, the chelating agent is citric acid or a salt thereof, ethylenediaminetetraacetic acid (EDTA) or a salt thereof, aminotris(methylene-phosphonic acid) (ATMP) or a salt thereof, 1,2-bis(o-aminophenoxy)ethane-N,N,N',N'-tetraacetic acid (BAPTA) or a salt thereof, a bipyridine, diethylenetriamine (DETA), 1,4,7,10-tetraazacyclododecane-1,4,7,10-tetraacetic acid (DOTA) or a salt thereof, diethylenetriaminepentaacetic acid (DTPA) or a salt thereof, diethylenetriamine penta(methylene phosphonic acid) (DTMP) or a salt thereof, ethylenediamine-N,N'-disuccinic acid (EDDS) or a salt thereof, ethylenediamine tetra(methylene phosphonic acid) (EDTMP) or a salt thereof, ethylene glycol-bis(3-aminoethyl ether)-N,N,N',N'-tetraacetic acid (EGTA) or a salt thereof, 1-hydroxyethane 1,1-diphosphonic acid (HEDP) or a salt thereof, gluconic acid or a salt thereof, iminodiacetic acid (IDA) or a salt thereof, nitrilotriacetic acid (NTA) or a salt thereof, oxalic acid or a salt thereof, polyaspartic acid (PASA) or a salt thereof, or triethylenetetramine (TETA) or a salt thereof.

In some embodiments, the potential masking agent is a divalent cation. In some such embodiments, the divalent cation is $Mg^{2+}$, $Zn^{2+}$, $Ca^{2+}$, or $Cu^{2+}$. In some embodiments, the test sample further includes a second potential masking agent that is a nucleic acid. In some such embodiments, the nucleic acid is DNA or RNA. In some such embodiments, the DNA is extracted from a bacterial plasmid. In some embodiments, the nucleic acids are micro-nucleic acids or small interfering nucleic acids. In other embodiments, the nucleic acids are synthetic derivatives, including peptide nucleic acid, morpholino- and locked nucleic acid, as well as glycol nucleic acid and threose nucleic acid.

In some embodiments, the potential masking agent is a protein. In some such embodiments, the method further includes the step of contacting the test sample with a protease. In some such embodiments, the step of contacting the test sample with a protease is performed before the step of contacting the liquid crystal microdomains with the test sample.

In some embodiments, the potential masking agent is a nucleic acid. In some such embodiments, the nucleic acid is DNA or RNA. In some such embodiments, the DNA is extracted from a bacterial plasmid. In some embodiments, the nucleic acids are micro-nucleic acids or small interfering nucleic acids. In other embodiments, the nucleic acids are synthetic derivatives, including peptide nucleic acid, morpholino- and locked nucleic acid, as well as glycol nucleic acid and threose nucleic acid. In some embodiments, the test sample further includes a second potential masking agent that is a divalent cation. In some such embodiments, the divalent cation is $Mg^{2+}$, $Zn^{2+}$, $Ca^{2+}$, or $Cu^{2+}$.

In some embodiments, the liquid crystal within the dispersed liquid crystal microdomains is 4'-pentyl-4-cyanobiphenyl (5CB). In other embodiments, the liquid crystal is a nematic liquid crystal. In some embodiments, the liquid crystal microdomains are liquid crystal droplets. In some such embodiments, the liquid crystal droplets have a minor axis of from about 1 μm to about 10 μm.

In a third aspect, the disclosure encompasses a method for quantifying an analyte in a test sample. The method includes the steps of (a) contacting a plurality of dispersed liquid crystal microdomains having one or more point defects with a test sample, wherein the test sample includes a potential masking agent selected from the group consisting of a non-ionic surfactant, a chelating agent, a divalent cation, a protein, a nucleic acid, and combinations thereof; and (b) determining the configuration of the liquid crystal in the liquid crystal microdomains. The percentage of liquid crystal microdomains exhibiting a particular configuration is correlated with the quantity of analyte in the test sample.

In some embodiments, the liquid crystal microdomains have a minor axis of between about 0.5 μm and about 200 μm.

In some embodiments, the particular configuration is a bipolar configuration or radial configuration. In some such embodiments, the bipolar configuration corresponds to a liquid crystal microdomain having two point defects, and the radial configuration corresponds to a liquid crystal microdomain having one point defect.

In some embodiments, the percentage of liquid crystal microdomains having a particular configuration, including without limitation the radial configuration, is directly correlated with the quantity of analyte in the test sample.

In some embodiments, the quantity of analyte in the test sample is expressed as the concentration of analyte in the test sample.

In some embodiments, the step of determining the configuration of the liquid crystal in the liquid crystal microdomains is performed by one or more of optical imaging, fluorescence imaging, optical imaging using polarized light, polarized light microscopy, bright field microscopy, fluorescence microscopy, light scattering measurement, flow cytometry, fluorescence flow cytometry, microelectrophoresis, dielectrophoresis, measurement of electrical capacitance, measurement of magnetic properties, measuring turbidity, detecting optical reflection, detecting transmittance of light, visual inspection, using a plate reader, using microwell plates, using a flow focusing device, using a microfluidic channel, or using a cuvette in a detector.

In some embodiments, the test sample further includes an analyte. In some such embodiments, the concentration of the analyte in the test sample is less than 1 μM. In some embodiments, the analyte is endotoxin lipopolysaccharide (LPS) or the lipid A part of LPS.

In some embodiments, the potential masking agent is a non-ionic surfactant. In some such embodiments, the non-ionic surfactant is Sorbitan monolaurate, Sorbitan monopalmitate, Sorbitan monostearate, Sorbitan mono-oleate, Sorbitan trioleate, Polyoxyethylene (20) sorbitan monolaurate, Polyoxyethylene (20) sorbitan monopalmitate, Polyoxyethylene (20) sorbitan monostearate, Polyoxyethylene (20) sorbitan mono-oleate, Polyoxyethylene (20) sorbitan tristearate, Polyoxyethylene (20) sorbitan tri-oleate, Triton X-100, Triton X-114, Triton X-405, Brij 30, Brij35, Brij 56, Brij 58, Brij78, Monolaurin, Nonoxynol-9, Pluronic P-123, Pluronic F-127, Cocamide DEA, or Cocamide MEA. In some embodiments, the test sample further includes one or more buffers. In some embodiments, the one or more buffers include one or more buffering salts. In some embodiments, the buffering salts include citrate or phosphate ions.

In some embodiments, the potential masking agent is a chelating agent. In some such embodiments, the chelating agent is citric acid or a salt thereof, ethylenediaminetetracaetic acid (EDTA) or a salt thereof, aminotris(methylenephosphonic acid) (ATMP) or a salt thereof, 1,2-bis(o-aminophenoxy)ethane-N,N,N',N'-tetraacetic acid (BAPTA) or a salt thereof, a bipyridine, diethylenetriamine (DETA), 1,4,7,10-tetraazacyclododecane-1,4,7,10-tetraacetic acid (DOTA) or a salt thereof, diethylenetriaminepentaacetic acid (DTPA) or a salt thereof, diethylenetriamine penta(methylene phosphonic acid) (DTMP) or a salt thereof, ethylenediamine-N,N'-disuccinic acid (EDDS) or a salt thereof, ethylenediamine tetra(methylene phosphonic acid) (EDTMP) or a salt thereof, ethylene glycol-bis(3-aminoethyl ether)-N,N,N',N'-tetraacetic acid (EGTA) or a salt thereof, 1-hydroxyethane 1,1-diphosphonic acid (HEDP) or a salt thereof, gluconic acid or a salt thereof, iminodiacetic acid (IDA) or a salt thereof, nitrilotriacetic acid (NTA) or a salt thereof, oxalic acid or a salt thereof, polyaspartic acid (PASA) or a salt thereof, or triethylenetetramine (TETA) or a salt thereof.

In some embodiments, the potential masking agent is a divalent cation. In some such embodiments, the divalent cation is $Mg^{2+}$, $Zn^{2+}$, $Ca^{2+}$, or $Cu^{2+}$. In some embodiments, the test sample further includes a second potential making agent that is a nucleic acid. In some such embodiments, the nucleic acid is DNA or RNA. In some such embodiments, the DNA is extracted from a bacterial plasmid. In some embodiments, the nucleic acids are micro-nucleic acids or small interfering nucleic acids. In other embodiments, the nucleic acids are synthetic derivatives, including peptide nucleic acid, morpholino- and locked nucleic acid, as well as glycol nucleic acid and threose nucleic acid.

In some embodiments, the potential masking agent is a protein. In some such embodiments, the method further includes the step of contacting the test sample with a protease. In some such embodiments, the step of contacting the test sample with a protease is performed before the step of contacting the liquid crystal microdomains with the test sample.

In some embodiments, the potential masking agent is a nucleic acid. In some such embodiments, the nucleic acid is DNA. In some such embodiments, the DNA is extracted from a bacterial plasmid. In some embodiments, the test sample further includes a second potential masking agent that is a divalent cation. In some such embodiments, the divalent cation is $Mg^{2+}$, $Zn^{2+}$, $Ca^{2+}$, or $Cu^{2+}$.

In some embodiments, the liquid crystal within the dispersed liquid crystal microdomains is 4'-pentyl-4-cyanobiphenyl (5CB). In other embodiments, the liquid crystal is a nematic liquid crystal.

In some embodiments, the liquid crystal microdomains are liquid crystal droplets. In some such embodiments, the liquid crystal droplets have a minor axis of from about 1 μm to about 10 μm.

In a fourth aspect, the disclosure encompasses a method of making a liquid crystal-based system for detecting an analyte in a test sample. The method includes the steps of (a) generating a plurality of liquid crystal microdomains having one or more point defects that are dispersed within an aqueous phase of a composition comprising the liquid crystal and an aqueous solution, wherein the liquid crystal microdomains have a minor axis of between about 0.5 μm and about 200 μm; and (b) incorporating a surfactant into the aqueous phase of the composition at a concentration that is below the concentration required to trigger the radial configuration within the liquid crystal microdomains.

In some embodiments, the liquid crystal within the dispersed liquid crystal microdomains is 4'-pentyl-4-cyanobiphenyl (5CB) or a nematic liquid crystal.

In some embodiments, the liquid crystal microdomains are liquid crystal droplets.

In some embodiments, the liquid crystal droplets have a minor axis of from about 1 μm to about 10 μm.

In some embodiments, the composition is a liquid crystal emulsion.

In some embodiments, the surfactant is incorporated at a concentration of less than 1 mM. In some such embodiments, the surfactant is incorporated at a concentration of from about 1 μM to about 100 μM. In some such embodiments, the surfactant is incorporated at a concentration of from about 1 μM to about 20 μM.

In some embodiments, the surfactant is sodium dodecyl sulfate (SDS).

In some embodiments, the method is used to make the one or more dispersed liquid crystal microdomains referred to in the description of the other aspects of the disclosure.

In some embodiments, the method further includes the step of preparing a final test sample by incorporating a surfactant into a composition comprising an initial test sample at a concentration that is below the concentration required to trigger the radial configuration within the liquid crystal microdomains. In some such embodiments, the surfactant is incorporated into the test sample at a concentration of less than 1 mM. In some such embodiments, the surfactant is incorporated into the test sample at a concentration of from about 1 μM to about 100 μM. In some such embodiments, the surfactant is incorporated at a concentration of from about 1 μM to about 20 μM.

In some embodiments, the surfactant that is incorporated into the test sample is SDS.

In some embodiments, the surfactant is incorporated into the test sample at about the same concentration as it is incorporated into the composition comprising the liquid crystal and the aqueous solution.

In some embodiments, the method is used to make both the one or more dispersed liquid crystal microdomains and the test sample referred to in the description of the other aspects of the disclosure.

Other objects, features and advantages of the present invention will become apparent after review of the specification, claims and drawings.

BRIEF DESCRIPTION OF THE DRAWINGS

In FIG. 3A, the intensity of side light scattering (SSC-A) is plotted as a function of forward light scattering (FSC-A). In FIG. 3B, signal (droplet) count is plotted as a function of the intensity of forward light scattering (FSC-A). The patterns shown are those characteristic of bipolar configurations of LC droplets.

In FIG. 4A, the intensity of side light scattering (SSC-A) is plotted as a function of forward light scattering (FSC-A). In FIG. 4B, signal (droplet) count is plotted as a function of the intensity of forward light scattering (FSC-A). The patterns shown are those characteristic of radially oriented LC droplets.

In FIG. 12A, the intensity of side light scattering (SSC-A) is plotted as a function of forward light scattering (FSC-A). In FIG. 12B, signal (droplet) count is plotted as a function of the intensity of forward light scattering (FSC-A). The patterns shown are those characteristic of bipolar configurations of LC droplets.

In FIG. 13A, the intensity of side light scattering (SSC-A) is plotted as a function of forward light scattering (FSC-A). In FIG. 13B, signal (droplet) count is plotted as a function of the intensity of forward light scattering (FSC-A). The patterns shown are those characteristic of radially oriented LC droplets.

In FIG. 14A, the intensity of side light scattering (SSC-A) is plotted as a function of forward light scattering (FSC-A). In FIG. 14B, signal (droplet) count is plotted as a function of the intensity of forward light scattering (FSC-A). The patterns shown are those characteristic of radially oriented LC droplets, demonstrating the detection of the LPS by the LC droplets.

In FIG. 15A, the intensity of side light scattering (SSC-A) is plotted as a function of forward light scattering (FSC-A). In FIG. 15B, signal (droplet) count is plotted as a function of the intensity of forward light scattering (FSC-A). Note the similarity to FIGS. 14A and 14B, indicating that LC droplet-based detection of LPS is not affected by the presence of the divalent cation $Mg^{2+}$.

In FIG. 16A, the intensity of side light scattering (SSC-A) is plotted as a function of forward light scattering (FSC-A). In FIG. 16B, signal (droplet) count is plotted as a function of the intensity of forward light scattering (FSC-A). Note the similarity to FIGS. 14A and 14B, indicating that LC droplet-based detection of LPS is not affected by the combination of DNA and the divalent cation $Mg^{2+}$.

DETAILED DESCRIPTION

I. In General

Figure 1A:
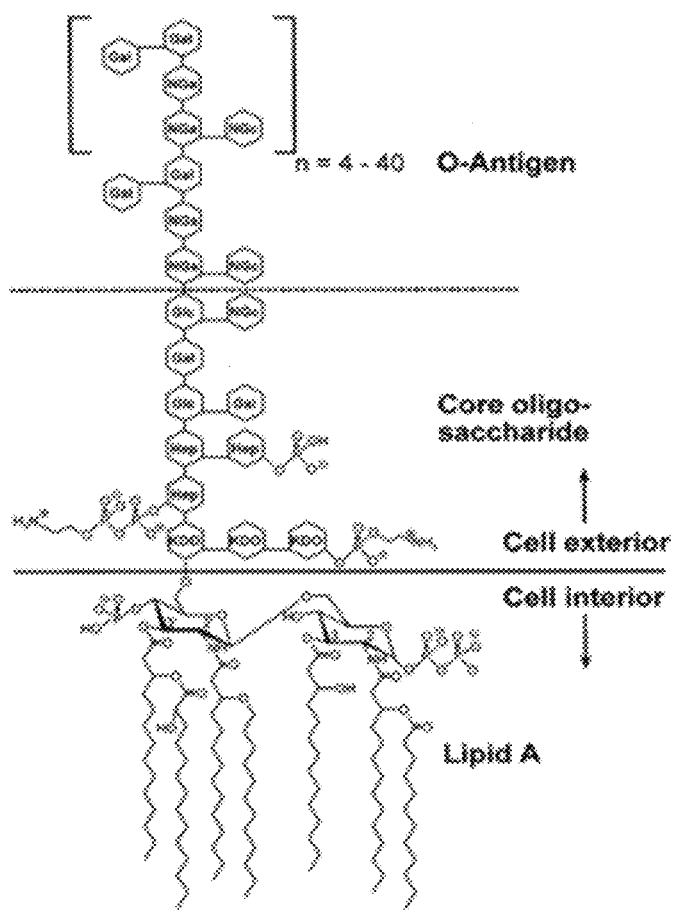
FIG. 1A shows a schematic representation of bacterial lipopolysaccharide (LPS), an endotoxin found in the outer membrane of Gram-negative bacteria.

Before the present materials and methods are described, it is understood that this disclosure is not limited to the particular methodology, protocols, materials, and reagents described, as these may vary. It is also to be understood that the terminology used herein is for the purpose of describing particular embodiments only, and is not intended to limit the scope of the invention.

As used herein and in the appended claims, the singular forms "a", "an", and "the" include the plural forms unless the context clearly dictates otherwise. As well, the terms "a" (or "an"), "one or more" and "at least one" can be used interchangeably, and the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art.

As used herein, "liquid crystal" means an organic composition in an intermediate or mesomorphic state between solid and liquid. Suitable liquid crystals for use in the present invention include, but are not limited to, thermotropic, polymeric, lyotropic, chromonic, smectic, nematic, ferroelectric and cholesteric liquid crystals.

A "microdomain" of liquid crystal refers to a volume of material in the liquid crystal phase defined by an interface wherein the volume has a minor axis that is not at any point larger than 200 μm across and the minor axis is defined as the shortest length across the volume of the liquid crystal.

The term "configuration" of the microdomain is used herein to describe the ordering of the liquid crystal within the microdomain, and is not used to imply the mechanism that leads to the ordering. In particular, it is not used to imply that the ordering results from the uniform adsorption of the analyte over the interface of the liquid crystal microdomain.

The term "defect" as used herein means a local region in a liquid crystal where the configurational order of the molecules in the liquid crystal is different from the surrounding region, as described in text books such as "The Physics of Liquid Crystals" by P. G. de Gennes. The core of a defect is typically nanoscopic in size, and scatters light. Locally, within the cores of most defects, the configurational order of the liquid crystal is low compared to the surrounding region. Defects can be lines (typically called disclination lines) or points in a liquid crystal, as well as other geometries (see text referenced above).

"LPS," also referred to interchangeably herein as "lipopolysaccharide" or "endotoxin," means a lipopolysaccharide comprised of a hydrophobic glycophospholipid region, called lipid A, and two polysaccharide portions (called the core polysaccharide chain and O-antigenic polysaccharide side chain) (see FIG. 1A). LPS is heterogeneous and strongly self-associating, with molecular weights ranging from 10-20 KDa. LPS is a constituent of the outer membrane of Gram-negative bacteria, and is released to the environment upon bacterial proliferation or death. The term LPS is used herein to include fragments of LPS, including without limitation the lipid A component of LPS.

Lipid A serves as a hydrophobic anchor of the LPS to the outer membrane of the Gram-negative bacteria. The minimal LPS structure required for the bacterial growth consists of lipid A and Kdo (3-deoxy-D-manno-oct-2-ulosonic acid) domain, although in wild-type bacterial strains, core polysaccharide chains and O-antigenic polysaccharide side chains may present. The lipid A architecture has been shown to be largely conserved between various Gram-negative bacterial strains, and both the self-associating tendency of the LPS and the capability of LPS to bind to host cell membranes is attributed to the lipid A component of the molecule. Variations in the structure of lipid A between bacteria can include the presence of 7 hydrophobic tails, rather than the 6 shown in FIG. 1A. The scope of the invention covers these variations in the structure of lipid A, and it is not restricted to the specific structure shown in FIG. 1A.

The core polysaccharide region of the LPS mainly consists of heptose resides (which often are substituted by phosphate or diphosphoethanolamine) in the "inner core" polysaccharide chains (lipid A proximal) and sugar components (D-glucose, D-galactose, D-glucosamine, D-galactosamine, or N-acetyl derivatives) in the "outer core" (O-antigen proximal). The repeating units of the "O-antigenic polysaccharide chain" consist of 1 to 8 sugars, with the entire chain containing up to 50 units.

"LPS free" means a medium that contains a concentration of LPS that is well below the concentration range of interest. For example, if the concentration range of LPS of interest in a sample is 100 pg/ml to 1000 pg/ml of LPS, then a buffer containing less than 0.1 pg/ml of LPS would be considered LPS free. Many buffers are commercially available that are sold as "LPS free." Some of these "LPS free" buffers are validated to contain less than 2 pg/ml of LPS. Such buffers are useful for dilution of samples that may contain concentration of LPS that are much greater than 2 pg/ml.

The following abbreviations are used throughout the present disclosure: LC, liquid crystal; LAL, *Limulus* Amoebocyte Lysate; LPS, lipopolysaccharide; 5CB, 4'-pentyl-4-cyanobiphenyl; PBS, phosphate buffered saline; SDS, sodium dodecyl sulfate.

II. The Invention

We have previously demonstrated that certain analytes, including without limitation LPS and lipid A, trigger configurational transitions upon contact with liquid crystal microdomains by changing the energies of topological point defects that are generated within such liquid crystal microdomains, rather than by the previously recognized mechanism of uniform adsorption over the aqueous interface of the liquid crystal microdomain. This mechanism for driving configurational transitions is exquisitely sensitive to the specific architecture of the analyte, providing the basis for extraordinarily sensitive sensors and methods for detecting certain analytes (see, e.g., U.S. Pat. Nos. 9,080,973, 9,341,571, and U.S. Patent Publication No. 2016/0223573, each of which is incorporated by reference herein in its entirety). However, it has never been shown that this previously disclosed method would work under conditions that can affect the accuracy of conventional LPS assays, such as in the presence of potential masking agents.

We have recently determined that the LC droplet-based methods previously disclosed in the '973 and '571 patents and in the '573 publication work just as well in the presence of potential masking agents that are known to affect the accuracy of conventional LAL-based assays. Such potential masking agents include, without limitation, non-ionic surfactants (that may optionally be present with one or more pH buffers such as citrate or phosphate), chelating agents, divalent cations, proteins, and/or nucleic acids. In the presence of potentially masking proteins, the method is modified to first expose the potentially masking protein to a protease (such as trypsin). This step digests the potentially masking protein, such that it does not affect the results of the assay.

As disclosed in the '973 and '571 patents and in the '573 publication, contacting an analyte such as LPS with micrometer-sized domains of LC (microdomains) triggers changes in the configuration of the LCs within the domains. In a particular embodiment, the domains of LC comprise LC droplets dispersed in an aqueous phase. The configurations of the LC domains and droplets (including the changes induced by LPS) can be determined in a low resource environment by visual inspection using polarized or bright field microscopy, or in a high through-put environment by using a continuous flow device such as a flow cytometer. As demonstrated in the '973 and '571 patents and in the '573 publication, a flow cytometer configured to measure light scattering (side scattering and/or forward scattering) can be used to quantify the number of liquid crystal droplets in a sample that exhibit radial and/or bipolar configurations. Measurements of electrical capacitance can also be used to determine the configuration of the liquid crystal within the microdomains.

Other methods of detection of the configurations of LCs within micrometer-sized domains and droplets are well known to those skilled in the art, including the use of fluorescent probes and dichroic dyes to report the ordering of the LC. The radial configuration of LC droplet can serve as a light wave guide, leading to fluorescent signatures of the LC droplets that permit distinction between radial and bipolar configurations. Thus, fluorescence intensity measurements and fluorescence microscopy can also be used to report the ordering of the LC in the micrometer sized domains. For example, many flow devices can report the fluorescent signature of micrometer-sized objects, including devices such as flow cytometers.

Accordingly, the present disclosure provides systems and methods for detecting and/or quantifying an analyte in a test sample that includes one or more potential masking agents by determining the configuration of one or more LC microdomains after exposing the LC microdomains to the test sample. As used herein, a droplet of LC is a type of microdomain of LC, but the disclosed LC microdomains are not limited to droplets of LC dispersed in aqueous solutions. Instead, the disclosure encompasses composite materials containing microdomains of LC, such as polymeric and inorganic materials. The microdomains of LC may be either mobile or immobile, and the scope of this disclosure covers both immobile and mobile droplets. In addition, the shape of the domain is not limited to a spherical shape. Shapes other than spherical, including hemispherical shapes formed by droplets on surfaces, are covered within the scope of this disclosure.

The disclosed systems and methods could be used for measuring LPS in situations where compounds that interfere with the LAL assay are present. It could also be used where high levels of automation are desired, the cost of the LAL assay is prohibitive, or where rapid analysis is needed. As demonstrated in the examples below and in the examples of the '973 and '571 patents and '573 publication, the volume ratio of test sample to liquid crystal emulsion (e.g., the concentration of LC droplets) can be tuned to maximize the sensitivity of the LPS detection method.

In the examples below, the liquid crystal used is 4-cyano-4'-pentylbipheny-1 (5 CB). These molecules can be assembled into a so-called nematic LC phase, where the molecules exhibit long-range orientational order that is not found in isotropic liquids. As the disclosed LCs are essentially ordered oils, emulsions containing droplets of nematic phase LC dispersed in aqueous phases can be created, or domains of LC can be contacted with aqueous phases without dissolution of the LC into the aqueous phase. A large number of methods can be used to create the LC dispersed phase, including sonication of LC in an aqueous phase, extrusion through a membrane, mechanical agitation, the use of a vortexing device and flow focusing, including flow focusing in microfluidic channels. In some embodiments, a concentration of surfactant below that which causes a configurational transition in the LC microdomains can be optionally added to the aqueous phase to facilitate the formation of the LC microdomains. An example of such a surfactant is sodium dodecylsulfate (SDS).

Within the microdomains of LC, the organization of the LC, known as the "configuration," depends both on the state of the interface between the LC and aqueous phase, the elastic energy associated with straining of the LC within the microdomain and the thermodynamics associated with the one or more point defects characteristic of the given configuration. Depending on the size of the microdomains, the structure, concentration and organization of any interfacial adsorbates, and the association of such adsorbates with any point defects present within the microdomains, the configuration of the LC within the microdomains can vary substantially, and this variation can be detected using optical and other detection methods. See Gupta et al. Angew. Chem. Int. Ed. 2008, 48, 1652-55. The configuration of the LC is dictated by the interfacial interactions of the LC as well as the energy stored in the volume of the LC droplets as a consequence of elastic strain of the LC.

Two configurations of LC droplets are commonly seen in the disclosed systems and methods. When the LC within the droplets anchor to the internal interface of the droplets with a tangential orientation, the configuration of the LC corresponds to a so-called "bipolar configuration." In contrast, if the LC assumes an orientation that is perpendicular to the interface, the configuration of the LC droplet changes to a "radial configuration."

Surprisingly, we have shown that contacting LPS with μm size LC droplets at the LC droplet interface can trigger the LC droplets to change very quickly from the "bipolar" to the "radial" configuration at remarkably low LPS concentrations, with a specificity that is high relative to other compounds commonly present in biological matrices, even in the presence of potential masking agents.

In one aspect, the disclosure encompasses a liquid crystal-based system for detecting an analyte in a test sample. The analyte is preferably but not limited to LPS or lipid A. The system includes one or more liquid crystal microdomains and a test sample that includes one or more potential masking agents in contact with the liquid crystal microdomains. Preferably, the microdomains are dispersed and have a minor axis of between about 0.5 μm and about 200 μm. More preferably, the liquid crystal microdomains have a minor axis of between about 1 μm and about 10 μm, and most preferably, the liquid crystal microdomains have a minor axis of between about 2 μm and about 4 μm. Although a variety of liquid crystals may be used in the invention, a preferred liquid crystal is 4'-pentyl-4-cyanobiphenyl (5CB).

The potential masking agents may include non-ionic surfactants, chelating agents, buffering salts, divalent cations, nucleic acids, and/or proteins, and combinations of these species.

Non-ionic surfactants are commonly used in a number of fields, including in formulating pharmaceutical compositions that may be subject to endotoxin assays. Any non-ionic surfactant can act as the potential masking agent in the disclosed systems and methods, particularly when present in combination with one or more buffering salts. Exemplary non-ionic surfactants that are commonly used are listed in Table 1 below. However, the disclosed systems and methods are not limited to those using these specific non-ionic surfactants.

TABLE 1

Exemplary Non-Ionic Surfactants

| | |
|---|---|
| 1 | Sorbitan monolaurate-Span 20 |
| 2 | Sorbitan monopalmitate-Span 40 |
| 3 | Sorbitan monostearate-Span 60 |
| 4 | Sorbitan mono-oleate-Span 80 |
| 5 | Sorbitan tristearate-Span 65 |
| 6 | Sorbitan trioleate-Span 8 |
| 7 | Polyoxyethylene (20) Sorbitan monolaurate-Tween 20 |
| 8 | Polyoxyethylene (20) Sorbitan monopalmitate-Tween 40 |
| 9 | Polyoxyethylene (20) Sorbitan monostearate-Tween 60 |
| 10 | Polyoxyethylene (20) Sorbitan mono-oleate-Tween 80 |
| 11 | Polyoxyethylene (20) Sorbitan tristearate-Tween 65 |
| 12 | Polyoxyethylene (20) Sorbitan tri-oleate-Tween 85 |
| 13 | Triton X-100 |
| 14 | Triton X-114 |
| 15 | Triton X-405 |
| 16 | Brij 30 |
| 17 | Brij 35 |
| 18 | Brij 56 |
| 19 | Brij 58 |
| 20 | Brij 78 |
| 21 | Monolaurin |
| 22 | Nonoxynol-9 |
| 23 | Pluronic P-123 |
| 24 | Pluronic F-127 |
| 25 | Cocamide DEA |
| 26 | Cocamide MEA |

The non-ionic surfactant may be present in the test sample in any concentration. In some embodiments, the non-ionic surfactant is present in the test sample in a concentration that causes low endotoxin recovery when using a standard LAL-based assay. In some embodiments, the concentration of the non-ionic surfactant in the test sample is greater than 0.001 (w/v) %, greater than 0.002 (w/v) %, greater than 0.004 (w/v) %, greater than 0.006 (w/v) %, greater than 0.008 (w/v) %, greater than 0.01 (w/v) %, greater than 0.02 (w/v) %, greater than 0.03 (w/v) %, greater than 0.04 (w/v) %, greater than 0.05 (w/v) %, greater than 0.06 (w/v) %, greater than 0.08 (w/v) %, or greater than 0.1 (w/v) %. In some embodiments, the concentration of the non-ionic surfactant in the test sample is from 0.001 (w/v) % to 1 (w/v) %, from 0.001 (w/v) % to 0.5 (w/v) %, from 0.002 (w/v) % to 0.5 (w/v) %, from 0.005 (w/v) % to 0.5 (w/v) %, from 0.01 (w/v) % to 0.5 (w/v) %, from 0.01 (w/v) % to 0.4 (w/v) %, from 0.02 (w/v) % to 0.2 (w/v) %, or from 0.04 (w/v) % to 0.2 (w/v) %. In some embodiments, the concentration of non-ionic surfactant in a test sample is lowered by dilution into aqueous solution prior to contact with the LC microdomains.

In some embodiments, the non-ionic surfactant is present in the test sample along with one or more buffers. Any buffer known in the art can be used in the test sample, including without limitation the exemplary buffers and buffer systems listed in Table 2 and Table 3 below.

TABLE 2

Exemplary Buffer Systems

| SI No. | Buffering system | pH range at 25° C. |
|---|---|---|
| 1 | Hydrochloric acid/Potassium chloride | 1.0-2.2 |
| 2 | Glycine/Hydrochloric acid | 2.2-3.6 |
| 3 | Potassium hydrogen phthalate/Hydrochloric acid | 2.2-4.0 |
| 4 | Citric acid/Sodium citrate | 3.0-6.2 |
| 5 | Sodium acetate/Acetic acid | 3.7-5.6 |
| 6 | Potassium hydrogen phtaalate/Sodium hydroxide | 4.1-5.9 |
| 7 | Disodium hydrogen phthalate/Sodium dihydrogen orthophospate | 5.8-8.0 |
| 8 | Dipotassium hydrogen phthalate/Potassium dihydrogen orthophospate | 5.8-8.0 |
| 9 | Potassium dihydrogen orthophophate/sodium hydroxide | 5.8-8.00 |
| 10 | Barbitone sodium/Hydrochloric acid | 6.8-9.6 |
| 11 | Tris (hydroxylmethyl) aminomethane/Hydrochloric acid | 7.0-9.00 |
| 12 | Sodium tetraborate/Hydrochloric acid | 8.1-9.2 |
| 13 | Glycine/Sodium hydroxide | 8.6-10.6 |
| 14 | Sodium carbonate/Sodium hydrogen carbonate | 9.2-10.8 |
| 15 | Sodium tetraborate/Sodium hydroxide | 9.3-10.7 |
| 16 | Sodium bicarbonate/Sodium hydroxide | 9.60-11.0 |
| 17 | Sodium hydrogen orthophosphate/Sodium hydroxide | 11.0-11.9 |
| 18 | Potassium chloride/Sodium hydroxide | 12.0-13.0 |

TABLE 3

Exemplary Buffers Used in Biological Systems

| Buffer | Structure of the Compound | pK$_a$ at 25° C. | pH Range |
|---|---|---|---|
| TAPS | (structure shown) | 8.43 | 7.7-9.1 |

TABLE 3-continued

Exemplary Buffers Used in Biological Systems

| Buffer | Structure of the Compound | p$K_a$ at 25° C. | pH Range |
|---|---|---|---|
| Bicine | | 8.35 | 7.6-9.0 |
| Tris | | 8.06 | 7.5-9.0 |
| Tricine | | 8.05 | 7.4-8.8 |
| TAPSO | | 7.635 | 7.0-8.2 |
| HEPES | | 7.48 | 6.8-8.2 |
| TES | | 7.40 | 6.8-8.2 |
| MOPS | | 7.20 | 6.5-7.9 |
| PIPES | | 6.76 | 6.1-7.5 |
| Cacodylate | | 6.27 | 5.0-7.4 |

TABLE 3-continued

Exemplary Buffers Used in Biological Systems

| Buffer | Structure of the Compound | pK$_a$ at 25° C. | pH Range |
|---|---|---|---|
| MES | (structure shown) | 6.15 | 5.5-6.7 |

The one or more buffers may be present in the test sample in any concentration. In some embodiments, the concentration of the one or more buffers in the test sample is greater than 0.01 mM, greater than 0.05 mM, greater than 0.1 mM, greater than 1 mM, greater than 5 mM, greater than 10 mM, greater than 50 mM, or greater than 100 mM. In some embodiments, the concentration of the non-ionic surfactant in the test sample is from 0.01 mM to 100 mM, from 0.01 mM to 50 mM, from 0.02 mM to 50 mM, from 0.05 mM to 50 mM, from 0.1 mM to 50 mM, from 0.1 mM to 40 mM, from 0.2 mM to 20 mM, or from 1 mM to 20 mM.

In some embodiments, the potential masking agent is a chelating agent, which is made up of molecules that can form several bonds to a single metal ion (i.e., having a multidentate ligand). Thus, chelating agents are capable of sequestering one or metal ions within a solution or removing such metal ions from a solution. A large number of chelating agents are known are known in the art, and any chelating agent or chelating agent combination can act as the potential masking agent or agents in the disclosed systems and methods. Exemplary chelating agents that are commonly used include citric acid or salts thereof, ethylenediaminetetraacetic acid (EDTA) or salts thereof, aminotris(methylenephosphonic acid) (ATMP) or salts thereof, 1,2-bis(o-aminophenoxy)ethane-N,N,N',N'-tetraacetic acid (BAPTA) or salts thereof, a bipyridine, diethylenetriamine (DETA), 1,4,7,10-tetraazacyclododecane-1,4,7,10-tetraacetic acid (DOTA) or salts thereof, diethylenetriaminepentaacetic acid (DTPA) or salts thereof, diethylenetriamine penta(methylene phosphonic acid) (DTMP) or salts thereof, ethylenediamine-N,N'-disuccinic acid (EDDS) or salts thereof, ethylenediamine tetra(methylene phosphonic acid) (EDTMP) or salts thereof, ethylene glycol-bis(β-aminoethyl ether)-N,N,N',N'-tetraacetic acid (EGTA) or salts thereof, 1-hydroxyethane 1,1-diphosphonic acid (HEDP) or salts thereof, gluconic acid or salts thereof, iminodiacetic acid (IDA) or salts thereof, nitrilotriacetic acid (NTA) or salts thereof, oxalic acid or salts thereof, polyaspartic acid (PASA) or salts thereof, and triethylenetetramine (TETA) or salts thereof. However, the disclosed systems and methods are not limited to those using these specific chelating agents.

The chelating agent may be present in the test sample in any concentration. In some embodiments, the concentration of the in the test sample is greater than 0.01 mM, greater than 0.05 mM, greater than 0.1 mM, greater than 1 mM, greater than 5 mM, greater than 10 mM, greater than 50 mM, or greater than 100 mM. In some embodiments, the concentration of the non-ionic surfactant in the test sample is from 0.01 mM to 100 mM, from 0.01 mM to 50 mM, from 0.02 mM to 50 mM, from 0.05 mM to 50 mM, from 0.1 mM to 50 mM, from 0.1 mM to 40 mM, from 0.2 mM to 20 mM, or from 1 mM to 20 mM.

Any known divalent cation can act as a potential masking agent in the disclosed systems and methods. Non-limiting examples include magnesium ion ($Mg^{2+}$), zinc ion ($Zn^{2+}$), calcium ion ($Ca^{2+}$), manganese ion ($Mn^{2+}$), and copper (II) ion ($Cu^{2+}$). The divalent may be present in the test sample in any concentration. In some embodiments, the divalent cation is present in the test sample at a concentration that affects the accuracy of the standard LAL-based assay. In some embodiments, the concentration of the divalent cation in the test sample is greater than 0.1 mM, greater than 0.2 mM, greater than 0.3 mM, greater than 1 mM, greater than 20 mM, greater than 50 mM, greater than 100 mM, or greater than 150 mM. In some embodiments, the concentration of the non-ionic surfactant in the test sample is from 0.1 mM to 300 mM, from 0.2 mM to 300 mM, from 0.2 mM to 200 mM, from 0.5 mM to 200 mM, from 1 mM to 200 mM, or from 50 mM to 200 mM.

Nucleic acids, such as DNA and RNA, can be used as a potential masking agent. In certain embodiments, the DNA is extracted from a bacterial plasmid. In some embodiments, the nucleic acids are synthetic strands, such as small interfering nucleic acids or micro-nucleic acids. In some such embodiments, the test sample also includes one or more divalent cations as potential masking agents. In some embodiments, the concentration of the nucleic acid in the test sample is greater than 0.1 μg/mL, greater than 0.2 μg/mL, greater than 0.5 μg/mL, greater than 1 μg/mL, greater than 10 μg/mL, greater than 50 μg/mL, greater than 100 μg/mL, or greater than 150 μg/mL. In some embodiments, the concentration of the nucleic acid in the test sample is from 0.1 μg/mL to 300 μg/mL, from 0.2 μg/mL to 300 μg/mL, from 0.2 μg/mL to 200 μg/mL, from 0.5 μg/mL to 200 μg/mL, from 1 μg/mL to 200 μg/mL, or from 50 μg/mL to 200 μg/mL.

Proteins, including without limitation known therapeutic proteins, can act as a potential masking agent in the disclosed systems and methods. Exemplary therapeutic proteins that may act as potential masking agents include infliximab, bevacizimab, belimumab, adalimumab, eculizumab, natalizumab, denosumab, ranibizumab, rituximab, omalizumab, tocilizumab, and golimumab. In certain embodiments, the protein is obtained from bacteria or from mammalian cells or from yeast cells, but the scope of the invention is not limited by the particular source of the protein. In some embodiments, the concentration of the protein in the test sample is greater than 0.001 μg/mL, greater than 0.01 μg/mL, greater than 0.1 μg/mL, greater than 1 μg/mL, greater than 10 μg/mL, greater than 50 μg/mL, greater than 100 μg/mL, or greater than 150 μg/mL. In some embodiments, the concentration of the nucleic acid in the test sample is from 0.001 μg/mL to 300 μg/mL, from 0.01 μg/mL to 300 μg/mL, from 0.1 μg/mL to 200 μg/mL, from 0.5 μg/mL to 200 μg/mL, from 1 μg/mL to 200 μg/mL, or from 50 μg/mL to 200 μg/mL.

In some embodiments using a protein as a potential masking agent, the protein is digested before the LC droplet-based assay is performed. In some embodiments, the protein is digested using a protease, such as trypsin. In a non-limiting example, the protease (e.g., trypsin) is immobilized onto beads (e.g., magnetic beads), which are then contacted with the test sample. This leads to the digestion of the potential masking protein into smaller fragments, which renders endotoxin, which may be masked by the original protein, detectable using the disclosed LC droplet-based methods.

In some embodiments, the system includes a detector capable of detecting the configurations of or the number of defects within the liquid crystal microdomains. In some embodiments, the liquid crystal microdomains possess topological defects prior to exposure of the liquid crystal microdomains to the analyte. In some embodiments, the liquid crystal microdomains possess two or more surface point defects prior to interaction with the analyte, and fewer point defects after interaction with the analyte to report the presence of the analyte. In some embodiments, the two or more point defects in the initial state of the liquid crystal are generated by confinement of the liquid crystal in non-planar geometries, including droplets, surface-supported droplets, microwells without limitation on the shapes of the microwells, and capillaries. The two or more defects can also be generated by the dispersing of solid objects in the liquid crystal, including colloidal particles which are well known to lead to the generation of topological defects in liquid crystals. A key aspect of the disclosure is that the interaction of the analyte such as LPS with the defective liquid crystal microdomains results in a change in the configuration of the liquid crystal and the number of defects within the liquid crystal, even in the presence of one or more potential masking agents.

Preferably, the number of defects in a liquid crystal microdomain may be determined by detecting the configuration of the liquid crystal within the microdomain. In a preferred embodiment, the two or more defects are generated in the liquid crystal by using liquid crystal microdroplets with two surface defects called Boojums in the bipolar configuration. The presence of the analyte is reported by a transition in the microdroplet configuration to a radial configuration where the single point defect at the center of the microdomain is stabilized by the analyte.

In some preferred embodiments, the liquid crystal microdomains are liquid crystal droplets dispersed in a liquid crystal emulsion. In some such embodiments, the liquid crystal emulsion is a liquid crystal in water emulsion where the aqueous phase is LPS free. In some embodiments, the water phase in which the liquid crystal is dispersed also contains concentrations of surfactant that are below that which cause the liquid crystal to assume a radial configuration.

In yet other embodiments, the dispersed liquid crystal microdomains are immobilized within the material containing the dispersed liquid crystal microdomains. In some such embodiments, microdomains may contain a polymer adsorbed to the surface of the microdomains. In certain of these embodiments, the microdomains are immobilized by either covalent bonding of the polymer to a separate solid surface or electrostatic forces between the polymer and the separate solid surface. In other embodiments in which the dispersed liquid crystal microdomains are immobilized, the material containing the dispersed liquid crystal microdomains may be dehydrated, and may include without limitation hydrophilic polymer networks or a gel formed from colloids or polymers. In some such embodiments, the invention further includes an absorbent material placed in contact with the material containing the dispersed liquid crystal microdomains.

In some embodiments, the liquid crystal microdomains are dispersed in water over a surface that contains depressions (wells), and the surfaces of the well are treated to generate a repulsive interaction between the well surface and the microdomains. This geometry confines the liquid crystal microdomains to the wells but prevent the adsorption of the microdomains onto the surface of the wells. This confinement can be useful to facilitate the read out of the configuration of the liquid crystal in the microdomains. In a preferred embodiment, the repulsive interactions are achieved by having like surface charges on the liquid crystal microdomains and the well surfaces. In a second embodiment, the repulsive interaction is created by the adsorption of polymers to the surfaces of the liquid crystal microdomains, the well surfaces or both.

A variety of different detectors may be used to detect the configuration of the liquid crystal microdomains. In some embodiments, the detector uses light-based detection. In some such embodiments, the detector may be a light-based imaging device, including without limitation a polarized light-based imaging device or a fluorescence-based imaging device. In other such embodiments, the detector may detect scattered light or transmitted light. In some embodiments, the detector includes a bright field light source.

In some embodiments, the detector is located on a flow device. A non-limiting example of a flow device on which the detector may be located is a flow cytometer. The flow cytometer may use a number of possible detection modes, including without limitation light scattering or fluorescence-based mode of detection.

Various liquid crystals may be employed in the dispersed liquid crystal drops of the present invention. Examples of suitable liquid crystals, include, but are not limited to, 4-cyano-4'-pentylbiphenyl (5 CB), 7 CB, and 8 CB, and E7 and TL205. A large listing of suitable liquid crystals is presented in "Handbook of Liquid Crystal Research" by Peter J. Collings and Jay S. Patel, Oxford University Press, 1997, ISBN 0-19-508442-X. Polymeric liquid crystals are also suitable for use in the device and methods of the present invention. Because the devices and methods of the present invention may include contacting the liquid crystal with aqueous test solutions, preferred liquid crystals employed in the invention should be insoluble in water or have very limited solubility in water. Additionally, preferred liquid crystals employed in the invention should not react with water.

In certain embodiments of the present invention, the liquid crystal comprising the droplets is 4-cyano-4'-pentylbipheny-1 (5 CB). Although various types of liquid crystal may be employed, nematic and thermotropic liquid crystals are preferred. However, smectic liquid crystals formed from 8 CB are also suitable for use in the present invention. Suitable liquid crystals further include smectic C, smectic C*, blue phases, cholesteric phases, smectic A, and polymeric liquid crystals.

Changes in liquid crystal ordering within liquid crystal droplets are influenced by the size of the droplets, reflecting a subtle competition between bulk and interfacial physiochemical factors (Gupta et al. Angew. Chem. Int. Ed. 2008, 48, 1652-55). In addition, the size of the droplets may be a factor in droplet coalescence and thus the stability of liquid crystal dispersions (Heppenstall-Butler et al. Liquid Crystals 2005, 32, 77-84). The preferred size for the liquid crystal microdomains of the present invention is a minor axis of between about 0.5 µm and about 200 µm, with a more preferred size being a minor axis of between about 1 µm and about 10 µm. The most preferred size for the liquid crystal droplets of the present invention is a minor axis of between about 2 µm and about 4 µm.

In certain embodiments, the material containing the dispersed liquid crystal droplets is an emulsion of liquid crystal droplets within another liquid, preferably within an aqueous buffer solution. The buffer solution should be LPS free, to prevent interference with the LPS assay. The aqueous solution may also be buffer free. Although a variety of standard buffer solutions would be suitable, a preferred LPS free buffer solution for use in the invention is phosphate buffered saline (PBS). In some preferred embodiments of the invention, the buffer solution will contain a concentration of a surfactant below that which causes the liquid crystal microdomains to transition to a radial configuration.

The volume ratio of the LC to the aqueous buffer solution in the LC emulsions of these embodiments can vary. However, it is preferred that the ratio of the initial volume of LC to the volume of aqueous buffer within the emulsion be substantially less than one to one, preferably less than about 1/10, and most preferably less than about 1/100.

In certain embodiments, the dispersed liquid crystal microdomains within the emulsion are immobilized on a substrate surface. Methods of immobilizing liquid crystal microdomains include without limitation the use of polymers (such as certain polymers having a structure that facilitates both (a) adsorption to a liquid crystal surface interface, and (b) the immobilization of the liquid crystal microdomain onto the substrate surface) to promote the immobilization of liquid crystal droplets on substrate surfaces. Such polymers can be spontaneously adsorbed to the droplet interface from the surrounding aqueous solution. An alternative approach which falls within the scope of the invention is to dissolve the polymer within the LC making up the microdomains, and to let it adsorb to the interface from the liquid.

The presence of the polymer at the interfaces of the droplets can be exploited to immobilize liquid crystal droplets on the substrate surface through covalent bond formation or through non-covalent interactions. Examples of non-covalent interactions that could be used to immobilize the liquid microdomains onto the substrate surface include without limitation electrostatic attractions, hydrophobic interactions, dative interactions, coordination bonds, metal-mediated interactions, or other interaction between the multifunctional polymer and the substrate surface.

In some embodiments, the immobilization of the LC microdomains to the substrate is further facilitated by the presence of a chemically functionalized surface on the substrate surface that is capable of interacting with the polymer adsorbed to the droplet interface. Further, the functionalized surfaces may be designed to pattern the immobilization of liquid crystal droplets on the surfaces as needed to further facilitate the present method.

In other embodiments, the material containing the dispersed liquid crystal microdomains is a solid or semi-solid. In some such embodiments, the LC droplets could be fixed within a material through which an aqueous test sample could flow, affecting the configuration of the fixed droplets as it contacts the droplets. Preferred materials for such embodiments are polymeric hydrogels that do not trigger a configuration change in LC droplets or a resulting optical response. As one skilled in the art would recognize, there are a number of ways such polymeric hydrogels containing dispersed liquid crystal droplets could be synthesized. One method to make such materials would be to cross-link a hydrogel about a dispersion of LC droplets using photo or chemical methods. Another approach would be to impregnate a hydrogel gel with isotropic mixture of a volatile solvent and LC-forming compound. Upon evaporation of the volatile solvent, the mesogen will phase separate to form LC droplets within the gel. This procedure is well-known in the art and is used to prepare dispersions of LC droplets in polymeric networks used in LC displays.

The gels may also be formed physically, such as through hydrogen bonding and hydrophobic interactions. Gels formed by amphiphile polymers such as pluronic polymers are suitable for these embodiments of the inventions. In other embodiments, the LC microdomains may be formed within a composite material, where one interface of the microdomains is exposed to the aqueous sample containing LPS. In a preferred embodiment the composite material is a colloid-in-liquid crystals gel comprised of micrometer-sized LC domains. In other preferred embodiments, the LC microdomains are supported on the surface of a solid material across which the LC domains do no spontaneously spread. An example of such a material is a silanized glass microscope slide that supports LC microdomains. In other embodiments the LC microdomains are defined by topographical features on surfaces, such as step edges and walls of microwells. In other preferred embodiments, electric fields and optical fields are used to trap or move the LC microdomains to enable detection of the analyte.

In certain embodiments using polymeric hydrogels, the hydrogel can be dehydrated using any of a number of dehydration methods known in the art. In these embodiments, rehydration of the hydrogel can be used to draw the aqueous test sample containing LPS into contact with the dispersed LC droplets. In other embodiments using polymeric hydrogels, the hydrogel can be hydrated prior to introduction of the sample, and an absorbent material can be placed downstream of the hydrogel in order to draw the sample across the dispersed LC droplets using capillary forces. In other embodiments, the sample can be placed onto the top surface of a material containing the LC microdomains, or the sample can be flowed through a microfluidic channel to contact the LC microdomains, or the sample can be placed into a well to contact the LC microdomains. In other embodiments, a device is contacted with an aqueous solution to remove LPS from the surface of the device, and LPS is detected within the aqueous solution by contact with micrometer-sized LC domains.

The liquid crystal-based system may also include a detector capable of detecting and reporting either the configuration of the liquid crystal microdomains or the number of defects in the liquid crystal microdomains, as described above. Because configuration of liquid crystal droplets can be determined using either polarized microscopy or bright field microscopy, an optical microscope can be used as the detector in certain embodiments.

More generally, the disclosure includes the use of polarized light or non-polarized light to detect the configuration of the LC within the droplet. Organized arrays of LC microdomains can also define optical band-gap materials and the scope of the disclosure includes use of such collective optical behaviors exhibited by arrays of LC microdomains. Because defects formed within the LC droplets scatter light, it is also possible to detect the configuration of LC within the LC microdomains by measurement of the scattering of non-polarized light. The light can be monochromatic, white light, or colored light comprising a mixture of wavelengths, and all can be employed.

The scope of the disclosure also includes the use of the LC microdomains as wave-guides. For example, by including one or more fluorescence molecules within the LC microdomain, it is possible to determine the configuration of the LC within the microdomain because the LC configuration will guide light to and from the fluorescence molecules. For example, the radial configuration of the LC droplet will guide light to the center of the droplet, and give rise to a bright fluorescence spot at the center of the droplet. The bright fluorescence spot can be used to detect that the droplet has assumed a radial configuration. Thus methods that detect fluorescence intensity and image fluorescence emissions fall within the scope of the current invention.

In a bipolar configuration, the director (local alignment of LC) follows the contour of the surface of the droplet, connecting the two diametrically opposed point defects (called boojums) at the poles of the LC droplets. The presence of two point defects in the bright-field image and the corresponding characteristic polarized image showing a relatively uniformly bright disk confirms the bipolar configuration in LC droplets.

In contrast, in a radial configuration, the director radiates from the center of the droplet and is normal to the interface. The LC droplet has one point defect located at the center of the droplet, which can be seen in a bright field image. When viewed under a polarized light microscope, the optical appearance of the radial configuration droplet is invariant when viewed at differing angles, and shows a characteristic isogyre (dark cross-shaped pattern), while the bipolar configuration does not. There is some evidence suggesting that the defect formed at the center of a radial configurational droplet may possess a complex nanostructure. However, the nanostructure is smaller than that which can be resolved with an optical microscope, and thus the defects appear as point defects when liquid crystal microdomains are viewed with visible light. The use of the term point defect in this patent should not be considered limiting in terms of the particular nanostructure of the defect as scales below those that can be optically resolved. It is possible, for example, that the local nanostructure of the point defects in the current invention correspond to nanoscopic rings that when viewed with far-field optics appear as point defects.

Accordingly, the detector used in certain aspects of the present invention may be an optical microscope that is fitted with specialized parts to enable the viewing of polarized or bright field images. Such parts may include, but are not limited to, bright field light sources appropriate for bright field microscopy and cross-polarizers for use in polarized microscopy. Other parts that may be used in such detectors would be readily recognized by those skilled in the art.

More generally, devices that optically probe the LC microdomains, and record a signature that changes with the internal configuration of LC within the LC microdomains can be used for the practice of this invention. These devices can comprise a flow channel, where the LC microdomains are introduced to the device through an inlet and removed through an outlet, or the devices can comprise a geometry that possesses a single inlet, such as a cuvette used in a spectrophotometer. The invention includes use of a spectrophometer to determine the configuration of the LC droplets through changes in the intensity of light that is transmitted through the LC domains. Such devices may also comprise one or more wells or microwells to contain the LC microdomains for optical probing.

In certain other embodiments, a fluidic reader such as a flow cytometer may be used as the detector in the liquid-crystal based sensor. In a flow cytometer, a beam of light is directed onto a hydro-dynamically focused stream of fluid, which could include the liquid crystal emulsion contained in certain embodiments of the invention. Multiple detectors are aimed at the point where the stream passes through the light beam, both in line with the light beam (measuring forward scatter or FSC) and perpendicular to the light beam (measuring side scatter or SSC). The liquid crystal droplets passing through the beam scatter the light both forward and to the side, and this scattering of light can be detected by analyzing the fluctuations in brightness at each detector.

The ratio of side-scattering to forward scattering of light in liquid crystal droplets undergoing flow cytometry analysis depends on the configuration of the droplets. In addition, the higher degree of symmetry present in the LC droplets having the radial configuration results in a tighter distribution of light scattering data for such droplets as compared to liquid crystal droplets having the bipolar configuration. This result is consistent with our present model of configuration, because light scattering from a radial droplet should be invariant to the rotation of the droplet, whereas the scattering from bipolar droplets depends on the configurations of the droplets and the incident light. The use of flow cytometry as a detector in the sensor of the present invention provides a rapid and high throughput method to detect and quantify the relative populations of radial and bipolar LC droplets, and thus to detect and quantify the LPS in a test sample. More generally, the scope of the disclosure includes measurement of the scattering of light from the LC domains to determine the configuration of the LC within the LC microdomains. A wide range of commercial devices permit measurement of scattering of light from objects, including light scattering instruments.

As the skilled artisan would recognize, there are additional types of detectors for detecting and reporting the configuration of the liquid crystal droplets. For example, as mentioned above, because of differences in fluorescence properties between liquid crystal droplets having the two configurations, a fluorescence-detecting flow cytometer or a fluorescence microscope may be used as a detector. In another example, because liquid crystals having different configurations have different dielectric properties, the detector may include an electrophoresis or dielectrophoresis apparatus or other device for applying an electric field. The configurations could then be detected by observing differences in movement of the liquid crystal droplets within the electrical field over time.

The disclosed systems and methods include a test sample that includes the potential masking agent placed in contact with the liquid crystal microdomains. The test sample is the solution that is to be tested for the presence and quantification of LPS. Varying the volume ratio of the LPS test sample to the liquid crystal in the microdomains (and thus the volume ratio of the test solution to the LC contained within an emulsion) substantially affects the sensitivity of the sensor. In particular, starving the LPS at the aqueous-LC interface by decreasing the number of LC emulsion droplets per unit volume of LPS test sample used in the system increases the sensitivity of the method.

In some embodiments, the LC is added directly to the sample and a dispersion of LC emulsion droplets is generated within the sample volume. In some embodiments, the emulsion of LC droplets is created by sonication, mechanical agitation, homogenization using a homogenizer, by vortexing, or passage of the sample containing LC through an emulsifier. Many machines are described in the existing literature for formation of emulsions, and use of these machines is contemplated within the context of this disclosure.

In a second aspect, the disclosure encompasses a method for detecting and/or quantifying an analyte, preferably endotoxin lipopolysaccharide (LPS) or lipid A, in a test sample, wherein the test sample includes one or more potential masking agents, as described above. The method includes providing one or more liquid crystal microdomains, preferably dispersed and having a minor axis of between about 0.5 µm and about 200 µm, contacting the microdomains with a test sample that includes one or more potential masking agents (preferably an aqueous test sample), and using a detector to detect the configuration of or to determine the number of defects in the liquid crystal microdomains. More preferably, the liquid crystal microdomains have a minor axis of between about 1 µm and about 10 µm, and most preferably, the liquid crystal microdomains have a minor axis of between about 2 µm and about 4 µm.

In some embodiments, the liquid crystal microdomains are provided in a liquid crystal in water emulsion, and the liquid crystal microdomains are liquid crystal droplets. A preferred volume ratio of the aqueous test sample to the liquid crystal contained within the liquid crystal emulsion is greater than or equal to about 100 to 1, a more preferred volume ratio of the aqueous test sample to the liquid crystal contained within the liquid crystal emulsion is greater than or equal to about 1,000 to 1, and a still more preferred volume ratio of the aqueous sample to the liquid crystal contained within the liquid crystal emulsion is greater than or equal to about 40,000 to 1. In certain such embodiments, the emulsion is LPS free, and the step of providing the liquid crystal in water may include providing an LPS free buffer. The LPS free buffer may optionally include the presence of surfactant at a concentration below that which causes the LC microdomains to adopt a radial configuration.

A variety of methods may be used to detect the configuration of the liquid crystal microdomains, including without limitation optical imaging, fluorescence imaging, optical imaging using polarized light, polarized light microscopy, bright field microscopy, fluorescence microscopy, light scattering measurement, flow cytometry, fluorescence flow cytometry, microelectrophoresis, dielectrophoresis, measurement of electrical capacitance, measurement of magnetic properties, measuring turbidity, detecting optical reflection, detecting transmittance of light, visual inspection, using a plate reader, using microwell plates, and using a cuvette in a detector. Further details are described in detail above in connection with the description of the liquid crystal-based system.

In further embodiments, the method includes an additional step of using a microfluidic device to deliver the sample to the detector. In yet other embodiments, all pipettes, plasticware, vessels, and other devices used in performing the method are LPS free.

In certain embodiments, the method is used to quantify the analyte, preferably LPS or lipid A, present in the test sample. This can be done in a number of ways. For example, the percentage of radial or bipolar configuration droplets after contact with the test solution depends on the quantity of LPS in the test solution. Accordingly, quantification could be done by correlating configuration percentages to the percentages obtained from standardized samples of known concentration. As one skilled in the art would appreciate, quantification of LPS is not limited to such direct correlation, and there would be many ways to quantify LPS in a test sample from detector data. As a non-limiting example, a computer program based on testing of LPS solutions of known concentration could be developed to analyze light scattering or fluorescence data from flow cytometry to directly calculate the quantity of LPS present in a test sample without calculating the percentages of droplets having a given configuration.

In some embodiments, additional steps are performed. For example, in the disclosed methods of detecting and/or quantifying an analyte in a test sample, the test sample may be aged (i.e., incubated) and/or diluted, or a composition containing a surfactant (a non-limiting example is sodium dodecyl sulfate, SDS) and/or a buffer may be added to the test sample. In some embodiments, protease is added to the test sample.

In some embodiments, the steps are performed in a specific order. In some embodiments, the test sample is aged before it is contacted with the dispersed liquid crystal microdomains. In some embodiments, the test sample is diluted before it is contacted with the dispersed liquid crystal microdomains. In some embodiments, a surfactant and/or buffer is added to the test sample before it is contacted with the dispersed liquid crystal microdomains. In some embodiments, protease is added to the test sample, and the sample is then allowed to age before it is contacted with the dispersed liquid crystal microdomains.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

U.S. Pat. No. 9,080,973 issued on Jul. 14, 2015 to Abbott et al., U.S. Pat. No. 9,341,571 issued on May 17, 2016 to Abbott et al, and U.S. Patent Publication No. 2016/0223573 published on Aug. 4, 2016, generally disclose procedures for using a plurality of liquid crystal droplets dispersed within a test sample to detect and quantify an analyte within the test sample. In certain embodiments, the analyte that is detected and quantified is endotoxin lipopolysaccharide. The presence of endotoxin is correlated with a change in configuration in the liquid crystal within the droplets from the bipolar to the radial configuration, even at very low concentrations. The quantity of endotoxin present is correlated with the percentage of liquid crystal droplets present that exhibit the radial configuration.

In the examples below, the general procedures disclosed in the '973 and '571 patents and '573 publication for detecting and quantifying endotoxin by detecting the change in configuration of the dispersed liquid crystal droplets from the bipolar to the radial configuration were followed. Accordingly, U.S. Pat. Nos. 9,080,973 and 9,341,571 and U.S. Patent Publication No. 2016/0223573 are each hereby incorporated by reference herein in its entirety and for all purposes, including for providing more detailed instructions for performing the methods disclosed in the examples below.

In general, the liquid crystal emulsions used in the Examples below were formed by sonicating and/or vortexing a mixture of 5CB with an aqueous solution, such as a PBS buffer. In one non-limiting example, twelve cycles of alternating 10-second vortex mixing (at 2500 rpm) and 10-second sonication resulted in milky white LC-in-PBS emulsions. The LC droplets of such emulsions are spherical, with a radius size range of 1-10 µm, and are visually observed to be stable against coalescence at least for 3 hours. The LC emulsions are preferably used within 3 hours of their formation, to avoid potential changes in the distribution of drop sizes associated with coalescence and ripening of the emulsions. A second method used to prepare the emulsions in the examples below involved the addition of 10 micromolar SDS to the aqueous PBS, and vortexing of the sample for 30 seconds. In a preferred embodiment, 6 uL of liquid crystal is added to 3 mL of the buffer to prepare the emulsion. These Examples are non-limiting, and other methods could be used to prepare liquid crystal emulsions.

In the examples below, the LC emulsions were contacted with endotoxin-containing or endotoxin-free test solutions, as described in more detail within each example. The configurations of the LC within the dispersed LC droplets were then determined and reported as a % radial calculation. "% radial" refers herein to the percentage of the total LC droplets present that exhibit a radial configuration (i.e., have one point defect). The remaining percentage of the total LC droplets present exhibit bipolar configuration (i.e., have two point defects).

In the examples below, the configuration of the LC within the dispersed LC droplets (and consequently the % radial configuration) was determined by flow cytometry. Using a flow cytometer in light scattering mode as a detector to distinguish between and to quantify LC droplets in radial and bipolar configurations is disclosed in, e.g., U.S. Pat. Nos. 9,080,973 and 9,341,571 and U.S. Patent Publication No. 2016/0223573, which are incorporated by reference herein. The ratio of side-scattering to forward scattering of light exhibited by the LC droplets, the measured forward scattering exhibited by the LC droplets, and the tightness of the distribution of both of these quantities are dependent on the internal configuration of the LC droplets. Thus, when LC droplets having radial and bipolar configurations are passed through a flow cytometer and side light scattering intensity (SSC) is plotted as a function of forward light scattering intensity (FSC) for the LC droplets, LC droplets exhibiting the two different configurations show distinctly different patterns that can be distinguished on a flow cytometry scatter plot. Furthermore, % radial configuration can be quantified from data showing the number of counts (i.e., droplets) detected as a function of the amount of forward scattering, as measured by flow cytometry. These Examples are non-limiting, and other methods could be used to determine the configuration of the LC within the dispersed LC droplets.

Example 1

Test Sample Buffer System Results in Low Endotoxin Recovery when Using the LAL Assay.

Figure 1B:
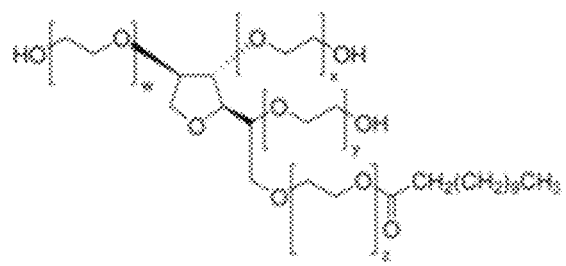
FIG. 1B shows the molecular structure of Tween 20, a non-ionic surfactant.

The LAL Assay is a standard method well-known in the art for quantifying endotoxin (FIG. 1A) in a test sample, such as a pharmaceutical formulation. Pharmaceutical formulations, including without limitations those formulated for delivery of one or more therapeutic proteins, commonly include non-ionic surfactants and buffers. In this Example, we illustrate low endotoxin recover (LER) when using the standard LAL Assay with a test sample that includes an exemplary non-ionic surfactant (Tween 20; FIG. 1B) and buffer (sodium citrate) combination.

An aqueous buffer system containing 0.05% Tween 20 (non-ionic surfactant) and 10 nM sodium citrate (buffer) was prepared. A negative control solution for LAL assay was obtained from a sample of the aqueous buffer to which no LPS was added (Control 1). A positive control solution for LAL assay was obtained from a sample of the aqueous buffer to which LPS was loaded at a concentration of 10 ng/mL (Control 2). The LAL assay was performed on both solutions. For Control 2, the LAL assay was performed immediately after LPS loading. For the negative control (Control 1), the LAL assay reported an LPS concentration of 0.002±0.001 ng/mL. For the positive control (Control 2), the LAL assay reported an LPS concentration of 10.4±4.7 ng/mL.

Figure 2:
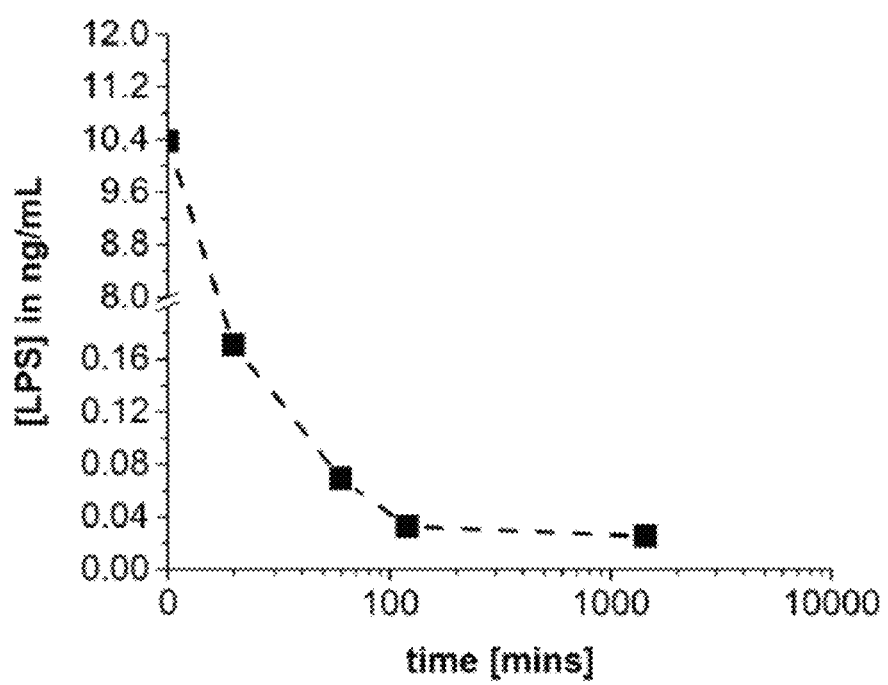
FIG. 2 is a graph illustrating low endotoxin recovery (LER) when using the LAL assay with a buffer system that includes 0.05% Tween 20 and 10 mM sodium citrate. [LPS] was loaded in all samples at a concentration of 10 ng/mL.

Additional samples were prepared from the aqueous buffer solution, loaded with LPS at the same concentration as Control 2. However, these samples were allowed to age before the LAL assay was performed. The LAL assay was performed on three different aged samples, one aged for one hour after LPS loading, one aged for two hours after LPS loading, and one aged for 24 hours after LPS loading. The results are shown in Table 4 below, along with the results obtained with Control 1 and Control 2, as reported above. Furthermore, FIG. 2 shows the reported [LPS] using the LAL assay as a function of sample aging time before the assay is performed.

TABLE 4

LPS concentrations reported in samples using standard LAL assay

| Samples | Average in ng/mL | Std Dlv. |
|---|---|---|
| No LPS (Control 1) | 0.0017 | 0.0008 |
| LPS in LAL water (Control 2) | 10.3773 | 4.7393 |
| LPS (20 mins) | 0.1707 | 0.2193 |
| LPS (1 hr) | 0.0692 | 0.0239 |
| LPS (2 hrs) | 0.0329 | 0.0048 |
| LPS (24 hrs) | 0.0253 | 0.0035 |

As reported in Table 4 and in FIG. 2, the LAL assay is unable to accurately report the known amount of purified LPS from the solution in the presence of Tween 20 and citrate buffer. The LER that substantially affects the accuracy of the assay is a time-dependent phenomenon. As seen in FIG. 1, surfactant/buffer conditions can lead to very fast masking kinetics. The complete masking of LPS requires less than one hour of aging, after which the endotoxin cannot be recovered.

The results disclosed in this example illustrate one of several limitations of the LAL assay in accurately quantifying LPS in certain samples. This limitation can be overcome by using the presently disclosed liquid crystal-based assay methods, which are not affected by the presence of non-ionic surfactants and/or buffers.

Example 2

Quantification of Endotoxin Using LC Emulsion Droplets does not Exhibit LER in the Presence of Non-Ionic Surfactant and Buffer.

This example shows that, unlike the standard LAL assay, the liquid crystal-based endotoxin quantification method previously disclosed in U.S. Pat. Nos. 9,080,973 and 9,341,571 and U.S. Patent Publication No. 2016/0223573 does not exhibit low endotoxin recovery with a test solution that includes an exemplary non-ionic surfactant (Tween 20) and an exemplary buffer (sodium citrate). Accordingly, the LC-based method maintains its accuracy in the presence of such agents, regardless of whether the test sample is significantly aged.

LPS test solutions having concentrations of 0.5 pg/mL, 1 pg/mL, 5 pg/mL, 10 pg/mL, 50 pg/mL, 100 pg/mL, 500 pg/mL, and 1000 pg/mL LPS (FIG. 5 bottom axis), were used in the first part of this Example. Each of these test solutions was divided into two separate samples, one containing an exemplary buffer system (10 mM sodium citrate, pH 7.5), and the other containing an exemplary non-ionic surfactant/buffer system (0.001 w/v % Tween 20, 10 mM sodium citrate, pH 7.5). We prepared LC emulsions by addition of 6 uL of 5CB to 3 mL of aqueous buffer containing 10 mM sodium citrate, pH 7.5 and 10 uM SDS. The LC emulsion was vortexed for 30 seconds to achieve the appropriate size distribution of the emulsion droplets. The emulsion was equilibrated 1 hr prior to use. Prior to contacting the samples with the LC emulsions, SDS was added to the samples to a concentration of 10 uM SDS. We contacted LC emulsion with each of these sixteen different LPS test solutions to obtain two different LC droplet concentrations for each test solutions: 500 droplets/µL and 5000 droplets/µL. The resulting liquid crystal configurations of the droplets (radial or bipolar) were determined for each of the 32 resulting systems using flow cytometry, and the % radial calculated and plotted as a function of [LPS].

Figure 3A:
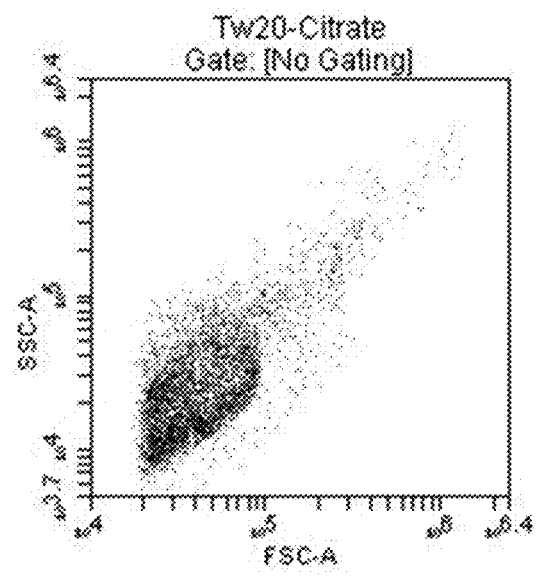
FIGS. 3A and 3B are scatter plots of flow cytometry data for a buffer system containing 10 mM sodium citrate, 0.001 w/v % Tween 20 and no LPS, pH 7.5.
Figure 3B:
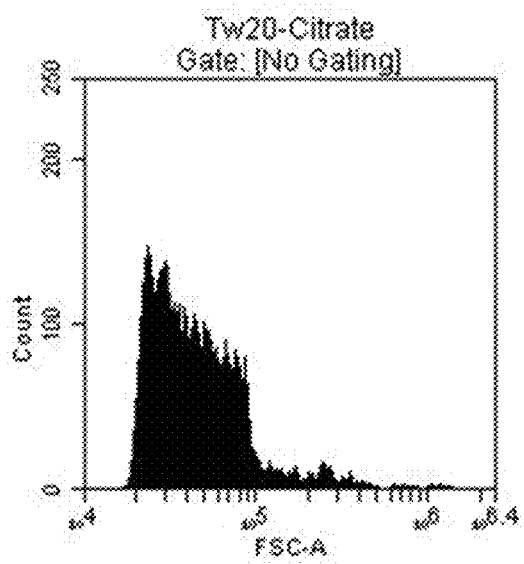
Figure 4A:
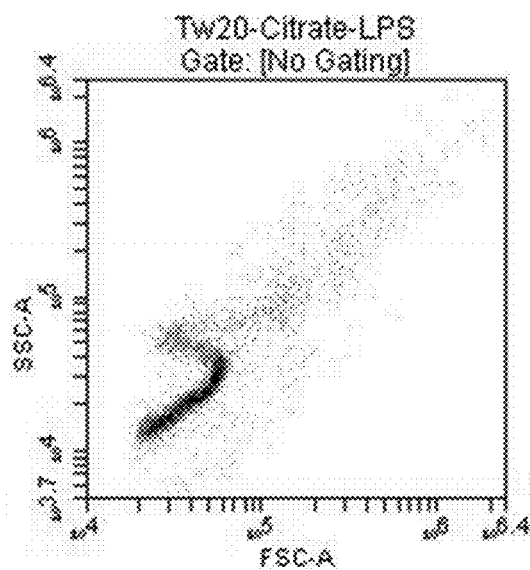
FIGS. 4A and 4B are scatter plots of flow cytometry data for a buffer system containing 10 mM sodium citrate, 0.001 w/v % Tween 20, and LPS at a concentration of 100 pg/mL, pH 7.5.
Figure 4B:
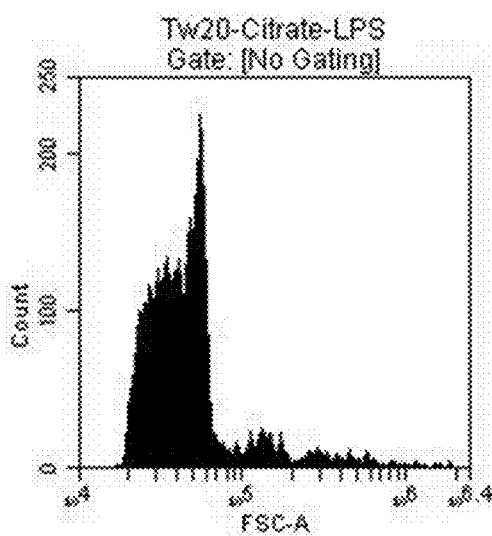

Scatter plots of raw flow cytometry data are shown in FIGS. 3A and 3B for a control sample containing 10 mM sodium citrate and 0.001 w/v % Tween 20 at pH 7.5, but no LPS. Scatter plots of raw flow cytometry data are shown in FIGS. 4A and 4B for the samples having an LPS concentration of 100 pg/mL. The LC droplet concentration in the samples used for these scatter plots was 5000 droplets/µL. The final results for all 32 LPS-containing systems are shown in FIG. 5.

FIG. 3A shows a flow cytometry side scattering to forward scattering intensity pattern that is characteristic of LC droplets having a bipolar configuration. Similarly, when the number of counts were plotted as a function of forward scattering intensity (FIG. 3B), the droplets showed a range of scattering intensities that is characteristic of LC droplets having a bipolar configuration. In contrast, FIG. 4A shows a 's-shaped' scatter plot with the narrower and downward-shifted distribution characteristic of droplets having the radial configuration, which is invariant to the rotation of the droplets. The narrowed range with a spiking forward scatter intensity shifted to a higher value that is seen in FIG. 4B is also characteristic of LC droplets exhibiting the radial configuration, a signal of the presence of LPS.

Figure 5:
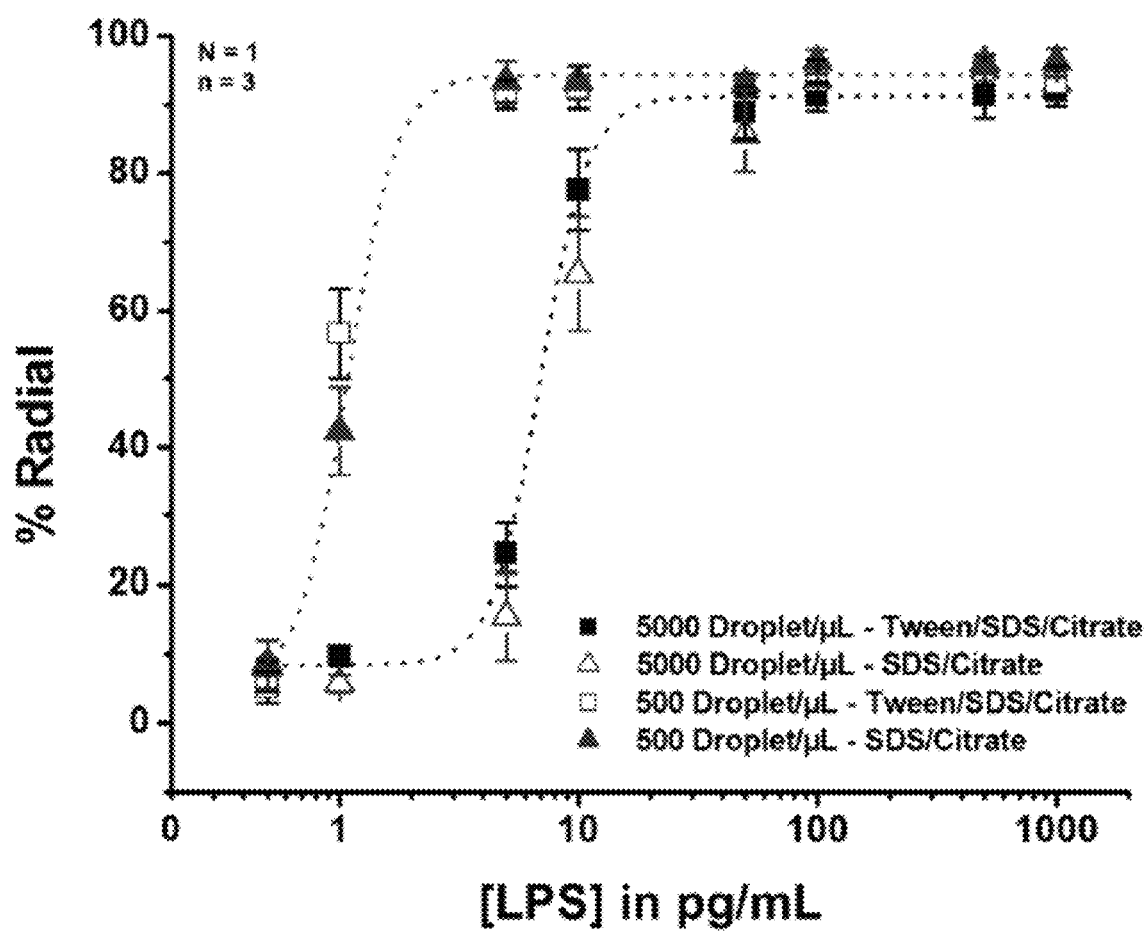
FIG. 5 is a graph showing LC droplet dose response to LPS with varying LC droplet count in Tween 20/Citrate buffer. Buffer system: 0.001 w/v % Tween 20/10 mM Sodium Citrate/10 μM SDS, pH 7.5; N=number of observations; n=number of replicates.

As seen in FIG. 5, quantification of endotoxin in solution in the pg/mL range leads to a dynamic response that is independent of the composition of the surfactant and buffer used (i.e., presence or absence of non-ionic Tween 20 surfactant). Accordingly, these results show that, unlike the LAL assay, the liquid crystal droplet-based assay is not affected by the composition of the surfactant/buffer system used. The results also confirm that the change in configuration of the liquid crystal droplets in response to endotoxin is dependent on the concentration of the liquid crystal droplets, with lower concentrations increasing the sensitivity of the method.

To demonstrate that unlike the standard LAL assay, the results of the liquid crystal droplet-based assay are independent of time (i.e., the aging of the test solution), LPS test solutions having concentrations of 0.0 pg/mL (no LPS), 100 pg/mL, 1 ng/mL, and 10 ng/mL LPS, were used. The LPS solutions (100 pg/mL, 1 and 10 ng/mL) contained 0.05% Tween 20/10 mM sodium citrate buffer (pH 7.5). After different incubation times, the solutions were then diluted 50× into SDS (10 uM)/sodium citrate buffer (10 mM, pH 7.5) to a final Tween 20 concentration of 0.001 w/v %. Subsequently, the samples were tested for LPS using LC emulsions prepared as described above. We note that after the 50× dilution, the concentration of LPS in the samples were 2 pg/mL, 20 pg/mL and 200 pg/mL, respectively. We added to each of these LPS test solutions a volume of the LC emulsion to obtain a LC droplet concentration of 5000 droplets/µL. The resulting liquid crystal configurations of the droplets (radial or bipolar) were determined using flow cytometry data for each of the systems at eleven different time points, and the % radial calculated and plotted as a function of time. The results are shown in FIG. 6.

Figure 6:
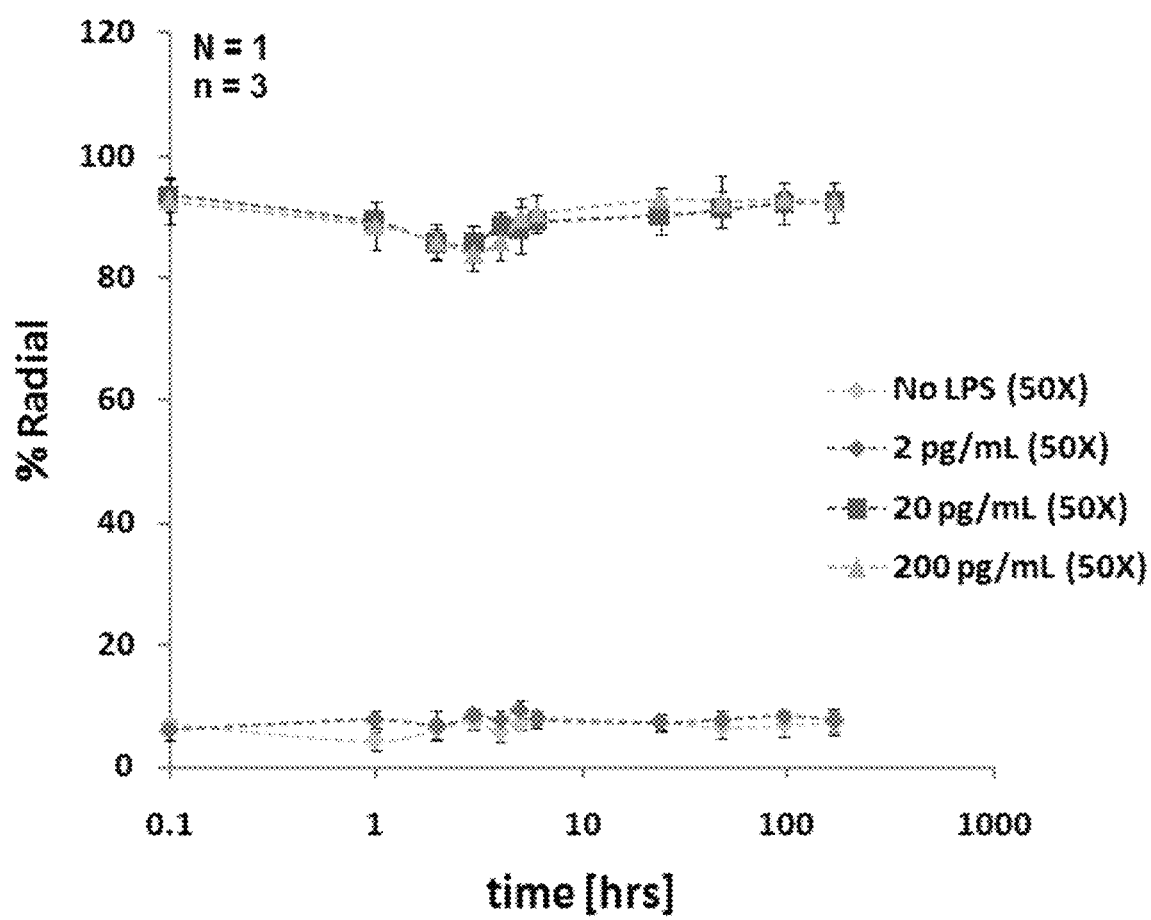
FIG. 6 is a graph showing time dependent response by LC assay. Buffer system: 10 mM Sodium Citrate/10 μM SDS/ 0.05 w/v % Tween 20, pH 7.5; N=number of observations; n=number of replicates.

As seen in FIG. 6, the assay responses are independent of time at all LPS concentrations obtained by the LC droplet-based assay. In contrast, the standard LAL assay is time-dependent in the presence of a non-ionic surfactant (see FIG. 1). This provides further evidence that the LC-droplet assay has certain advantages over the standard LAL assay.

Example 3

Quantification Using LC Emulsion Droplets is Independent of Endotoxin Source.

This example shows that, unlike the standard LAL assay, the liquid crystal-based endotoxin quantification method previously disclosed in U.S. Pat. Nos. 9,080,973 and 9,341,571 and U.S. Patent Publication No. 2016/0223573 is consistent regardless of the endotoxin source species or standard endotoxin type. This illustrates another advantage of the LC-based method over the standard LAL assay.

To demonstrate that the LC droplet based assay is consistent across multiple endoxin source species, test solutions comprising LPS from three different sources (*Esterichia coli, Salmonella minnesota*, and *Pseudomonas aeruginosa*) having eight different concentrations, were used (FIG. 5, bottom axis). In each of these test solutions, the LPS was incubated for two hours in a buffer system containing 10 mM sodium citrate, 10 µM SDS and 0.05 w/v % Tween 20, pH 7.5. The solutions were then diluted 50× to final [Tween 20]=0.001 w/v %. Therefore, after 50× dilution the final [LPS] in the test solutions were 0.0 pg/mL (control), 0.1 pg/mL, 2 pg/mL, 5 pg/mL, 10 pg/mL, 20 pg/mL, 200 pg/mL and 2000 pg/mL.

Figure 7:
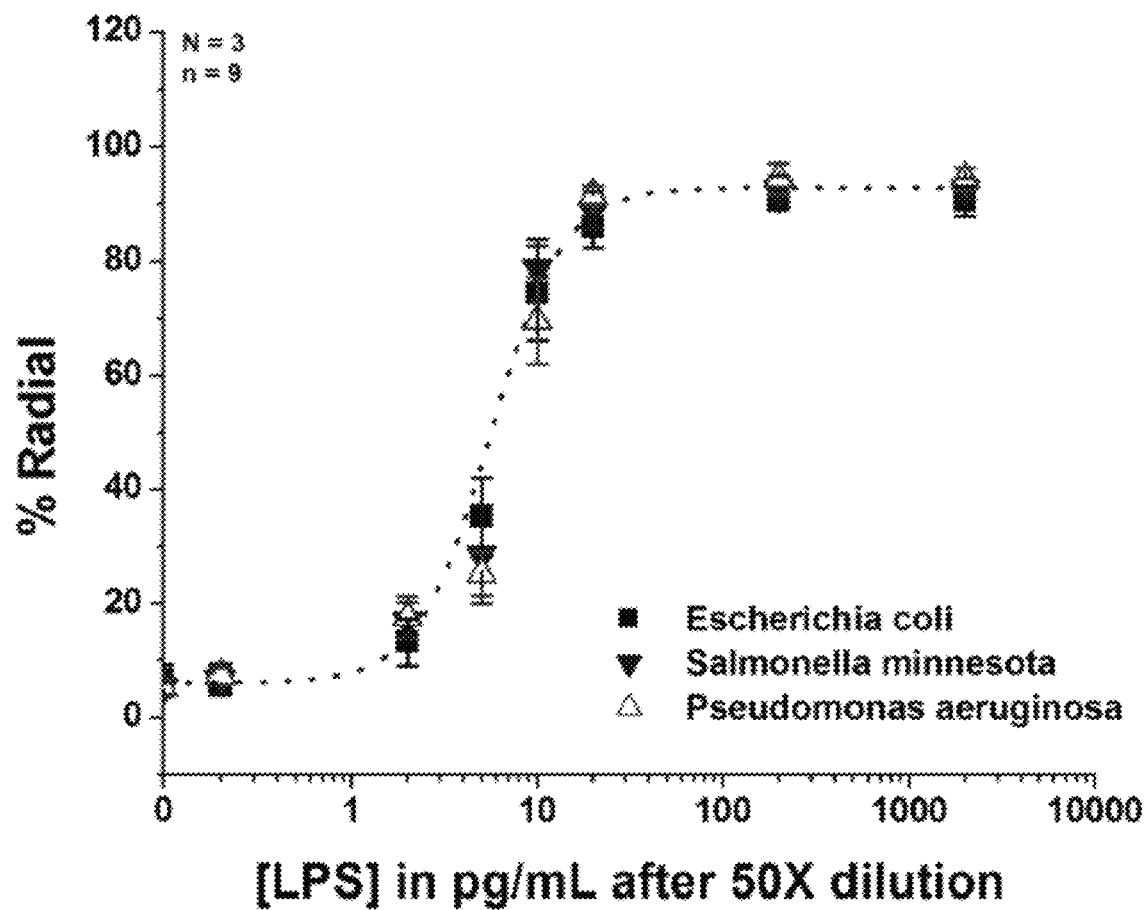
FIG. 7 is a graph showing LC droplet dose response to LPS from different sources in Tween 20/Citrate buffer. Buffer system: 10 mM Sodium Citrate/10 μM SDS/0.05 w/v % Tween 20, pH 7.5; N=number of observations; n=number of replicates.

We contacted LC emulsion with each LPS test solutions to obtain a LC droplet concentration of 5000 droplets/µL. The resulting liquid crystal configurations of the droplets (radial or bipolar) were determined for each of the resulting systems using flow cytometry data, and the % radial calculated and plotted as a function of [LPS]. The results are shown in FIG. 7. As seen in FIG. 7, quantification of endotoxin in solution was independent of the species source of the endotoxin.

Figure 8:
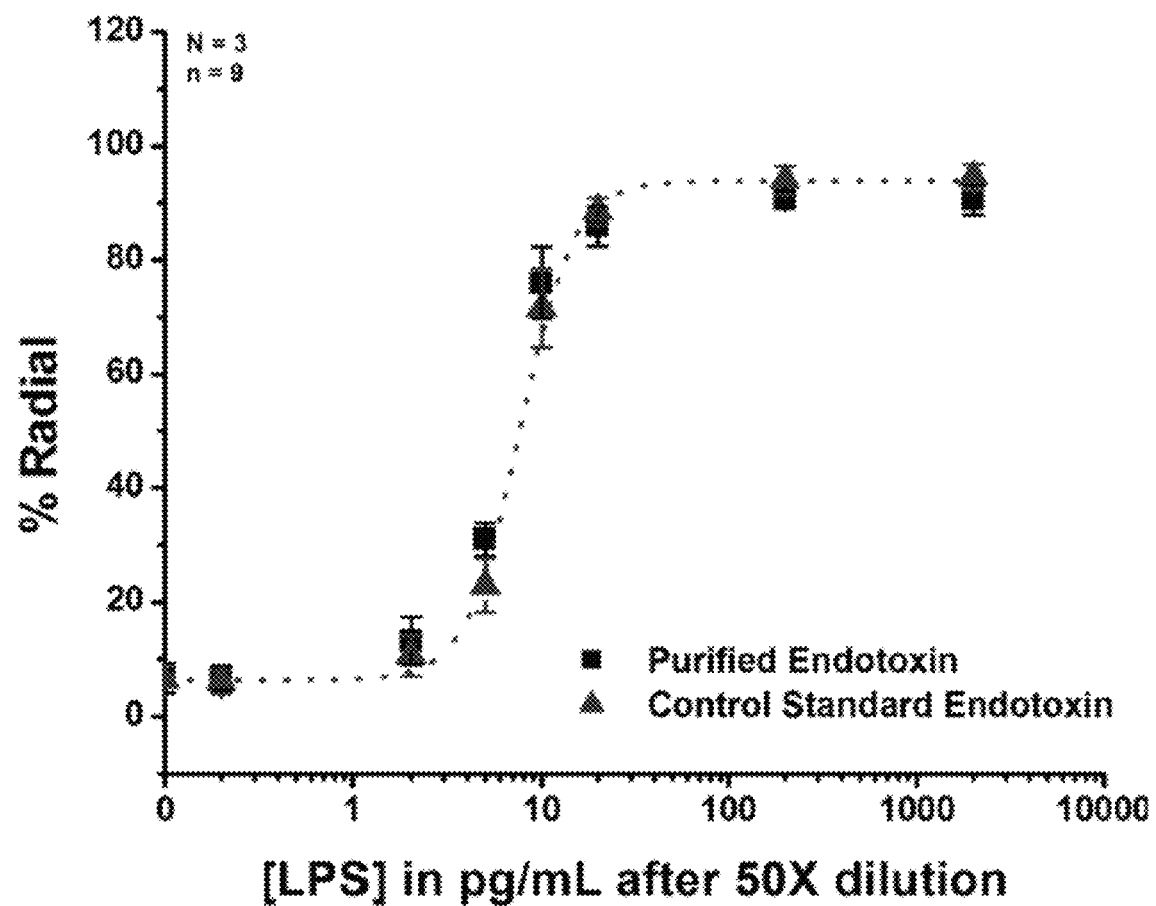
FIG. 8 is a graph showing LC droplet dose response to Control Standard Endotoxin (CSE) in Tween 20/Citrate buffer. Buffer system: 0.05 w/v % Tween 20/10 mM Sodium Citrate/10 μM SDS/, pH 7.5; N=number of observations; n=number of replicates. The samples were incubated in Tween 20/Citrate buffer for two hours.

To demonstrate that the LC droplet-based assay is consistent between Control Standard Endotoxin (CSE) and purified endotoxin, multiple endotoxin source species, test solutions comprising LPS from Purified Endotoxin and Control Standard Endotoxin (CSE) having eight different concentrations of LPS, were used (FIG. 8, bottom axis). In each of these test solutions, the LPS was incubated for two hours in a buffer system containing 10 mM sodium citrate, 10 µM SDS and 0.05 w/v % Tween 20, pH 7.5. The solutions were then diluted 50× to final [Tween 20]=0.001 w/v %. Therefore, after 50× dilution the final [LPS] in the test solutions were 0.0 pg/mL (control), 0.1 pg/mL, 2 pg/mL, 5 pg/mL, 10 pg/mL, 20 pg/mL, 200 pg/mL and 2000 pg/mL.

We contacted LC emulsion with each LPS test solutions to obtain a LC droplet concentration of 5000 droplets/µL.

The resulting liquid crystal configurations of the droplets (radial or bipolar) were determined for each of the resulting systems using flow cytometry data, and the % radial calculated and plotted as a function of [LPS]. The results are shown in FIG. 8. As seen in FIG. 8, CSE, which differs in form from purified endotoxin, exhibits a similar response in the LC droplet-based assay at pg/mL concentrations.

Taken together, these results show that the LC droplet-based assay has certain advantages regarding consistency when using LPS from different source or having different forms. This is in marked contrast to the standard LAL assay, which can show inconsistencies across different LPS forms or LPS source species.

Example 4

Reducing/Preventing Protein Interference in LC-Based Endotoxin Quantification.

This example illustrates a LC droplet-based method to detect and quantify endotoxin that can be successfully used in the presence of masking proteins that can prevent detection and accurate quantification of endotoxin when using conventional assay methods. This method represents an improved assay for endotoxin detection and quantification in compositions containing potentially masking proteins, including without limitation pharmaceutical compositions that contain therapeutic proteins.

The method uses protease to digest potentially interfering proteins into smaller fragments before using dispersed liquid crystal droplets to detect the endotoxin in the test sample. Specifically, three different test samples were prepared, each containing 100 pg/mL Endotoxin. The first (control) sample included no added protein. The second sample included added bovine serum albumin (BSA) at a concentration of 100 ng/mL. The third sample included added bovine serum albumin (BSA) at a concentration of 1 µg/mL.

Figure 9:
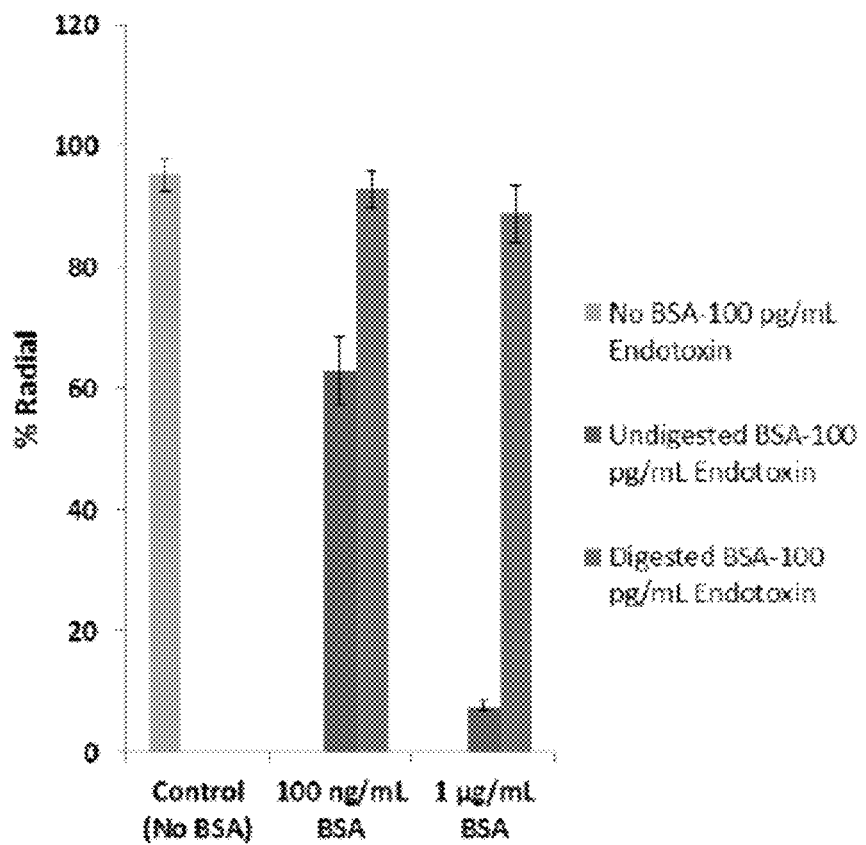
FIG. 9 is a graph showing detection of endotoxin (as measured by % LC droplets in the radial configuration) in samples with (100 ng/mL or 1 μg/mL) or without BSA masking protein, where the BSA masking protein was either undigested or digested with protease-functionalized beads.

We contacted LC emulsion with samples of each of the test solutions to obtain a LC droplet concentration of 5000 droplets/µL. The resulting liquid crystal configurations of the droplets (radial or bipolar) were determined for each of the three resulting systems using flow cytometry data, and the % radial calculated and plotted. The results are shown in FIG. 9 (No BSA–100 pg/mL endotoxin bar=control; Undigested BSA bars=two protein-containing samples). As seen in FIG. 9, the detection of endotoxin by LC configuration change from bipolar to radial was substantially reduced in the presence of undigested masking protein (BSA).

Next, fresh samples of the second and third (BSA-containing) test solutions were pretreated by contacting the solutions with protease (trypsin) functionalized magnetic beads. The solutions were incubated at 37° C. with vigorous mixing for 24 hours. The solutions containing proteolysis products of protein were then collected using a magnetic separator. The buffer used in these experiments was PBS. Prior to exposure of the digested samples to the LC emulsion, we added 10 uM of SDS to the samples. After that, we contacted LC emulsion (prepared as described above containing 10 uM SDS, and 10 mM PBS at pH 7.4) with each of the pretreated samples test solutions to obtain a LC droplet concentration of 5000 droplets/µL. The resulting liquid crystal configurations of the droplets (radial or bipolar) were again determined for each of the resulting systems using flow cytometry, and the % radial calculated and plotted.

As seen in FIG. 9, protease pretreatment largely eliminated the masking effect seen with the undigested BSA. Specifically, the digested (i.e., pretreated with protease) test samples exhibited a change in liquid crystal configuration that was comparable to that of the control sample. These results show that the LC droplet-based assay can be readily adopted to substantially reduce or eliminate the masking effect of any proteins present in the test sample. Thus, the LC droplet-based has certain advantages in assaying protein-containing pharmaceutical compositions.

Example 5

LC-Based Detection of Endotoxin in Plasmid DNA Samples and in the Presence of Divalent Cations.

This example illustrates that the LC droplet-based method can be successfully used to detect and quantify endotoxin in the presence of plasmid DNA and/or in the presence of divalent cations that are known to interfere with conventional endotoxin assays.

Plasmid DNA is used in transfection, gene therapy, microinjection, transplantation, vaccine and therapeutic drug production. Plasmid DNA typically is of bacterial origin, and when using standard isolation techniques, endotoxin may co-purify with the DNA. Endotoxin removal from plasmid DNA-based compositions, such as DNA vaccines, is very challenging.

Recent advancements in plasmid DNA (pDNA) production involve precipitation using a metal salt to selectively remove endotoxins from clarified cell lysates containing plasmid DNA. This presents potential problems in using the LAL assay, because endotoxins cannot be accurately assayed in samples that contain different types of metal ions, due to their strong effect on the LAL-chromogenic reaction. Specific examples of the effects of certain divalent cations on the accuracy of LAL-based assays have been noted in the background section of this application.

To demonstrate that, in contrast to the LAL assay, LC droplet-based methods are not affected by the presence of DNA or divalent cations, we first prepared test solutions comprising LPS having concentrations of 0.0 pg/mL (control), 0.5 pg/mL, 1 pg/mL, 5 pg/mL, 10 pg/mL, 50 pg/mL, 200 pg/mL and 2000 pg/mL LPS, were used (FIG. 8, bottom axis). Each of these test solutions were further divided into two test samples, one containing no DNA, and one containing 10 µg/mL DNA. The buffer used to prepare these samples was 1 mM sodium citrate (pH 6.0). Prior to adding the LC emulsion to these samples, 10 uM SDS was added to the samples.

Figure 10:
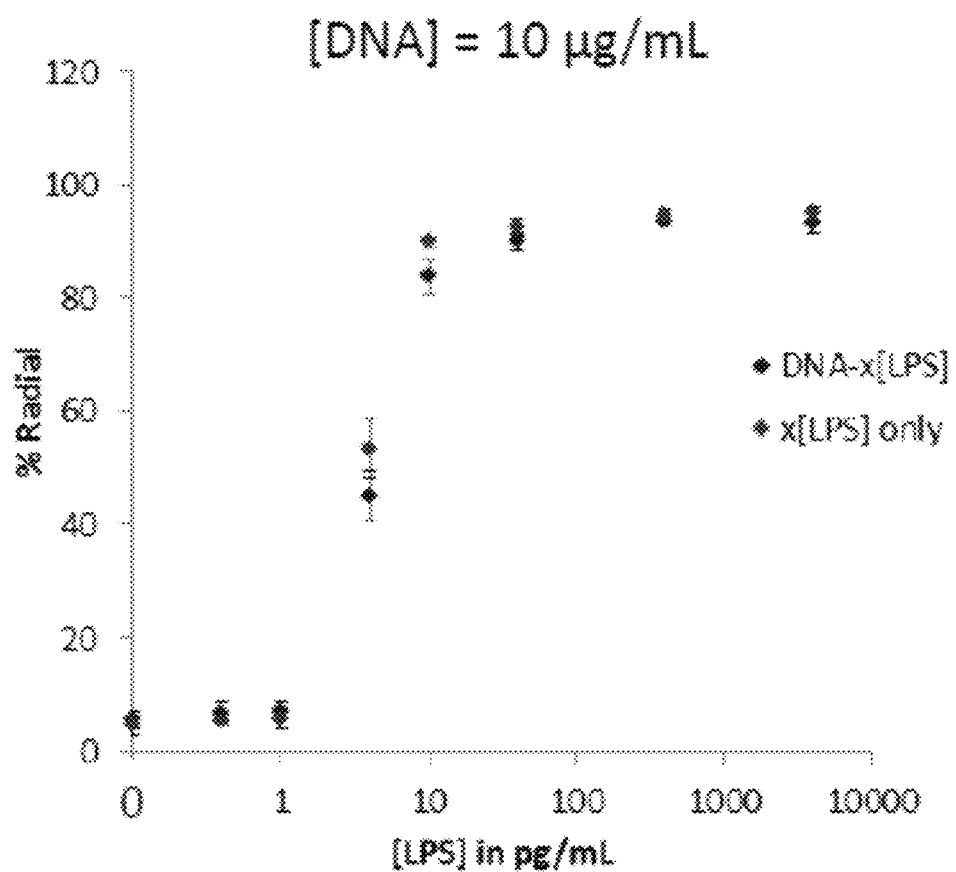
FIG. 10 is a graph showing LC droplet dose response to LPS in both the presence and absence of DNA. [DNA]=10 μg/mL.

We contacted LC emulsion (prepared as described above in buffer containing 1 mM sodium citrate, pH 6.0 with 10 uM SDS) with each of the test samples to obtain a LC droplet concentration of 5000 droplets/µL. The resulting liquid crystal configurations of the droplets (radial or bipolar) were determined for each of the samples using flow cytometry, and the % radial calculated and plotted as a function of [LPS]. The results are shown in FIG. 10. As seen in FIG. 10, the detection of endotoxin by LC configuration change from bipolar to radial was substantially similar in the presence or absence of DNA. These results indicate that DNA does not interfere with endotoxin detection/quantification when using LC-based assay methods.

To determine the effect of divalent salts on the disclosed LC droplet-based assays, we next measured the LC droplet response to LPS in the presence of different divalent salts in the both the presence and absence of DNA. Specifically, we first prepared four different test solutions. The first test solution (control 1) was a 1 mM citrate buffer (pH 6.0) that contained no LPS and no DNA. The second test solution (control 2) was a 1 mM citrate buffer (pH 6.0) that contained 10 μg/mL DNA and no LPS. The third test solution was a 1 mM citrate buffer (pH 6.0) that contained 40 pg/mL LPS and no DNA, and the fourth test solution was a 1 mM citrate buffer (pH 6.0) contained 40 pg/mL LPS and 10 μg/mL DNA.

Figure 11:
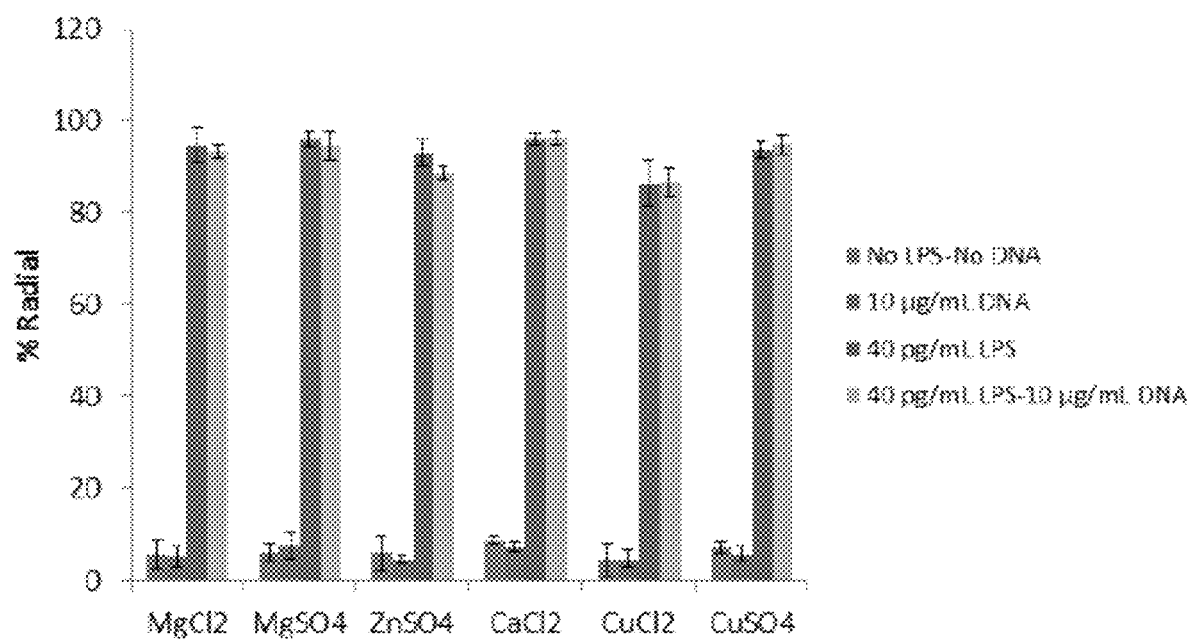
FIG. 11 is a graph showing LC droplet response with LPS-containing and LPS-free samples with or without DNA that further include one of six different salts containing a divalent metal cations. [DNA] (if present)=10 μg/mL; [LPS] (if present)=40 pg/mL; [salts]=100 mM.

Each of these four test solutions was further divided into separate test samples, to which was added a divalent cation-containing salt (magnesium chloride, magnesium sulfate, zinc sulfate, calcium chloride, copper (II) chloride, and copper (II) sulfate, respectively) to a final concentration of 100 mM or no divalent cation-containing salt. Prior to contact with the LC emulsion, SDS at a concentration of 10 uM was added to the samples. We contacted LC emulsion with each of the 28 test samples to obtain a LC droplet concentration of 5000 droplets/μL. The emulsion was prepared in 1 mM citrate buffer (pH 6.0) containing 10 uM SDS. The resulting liquid crystal configurations of the droplets (radial or bipolar) were again determined for each of the resulting systems using flow cytometry, and the % radial was calculated and plotted for the 24 test samples that included a divalent salt (FIG. 11). As seen in FIG. 11, no masking of LPS was exhibited in the presence of the divalent salts, either with or without plasmid DNA.

Figure 12A:
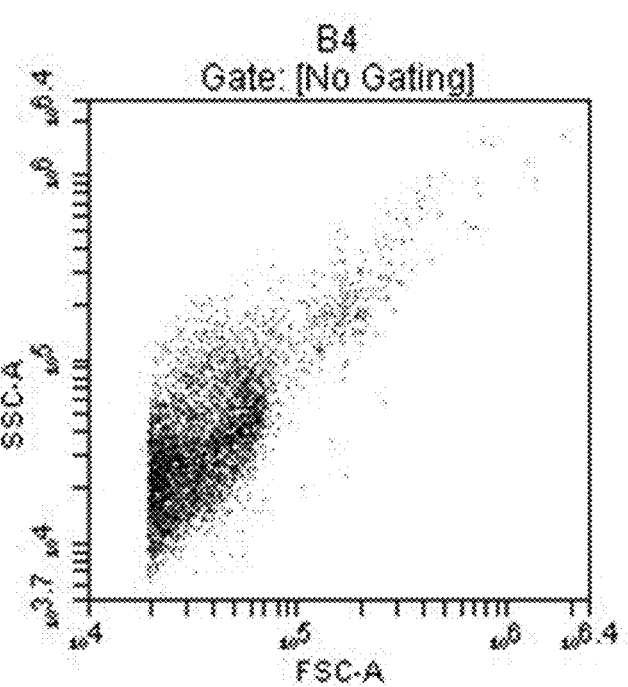
FIGS. 12A and 12B are scatter plots of flow cytometry data for a buffer system containing 1 mM citrate buffer at pH 6.0.
Figure 12B:
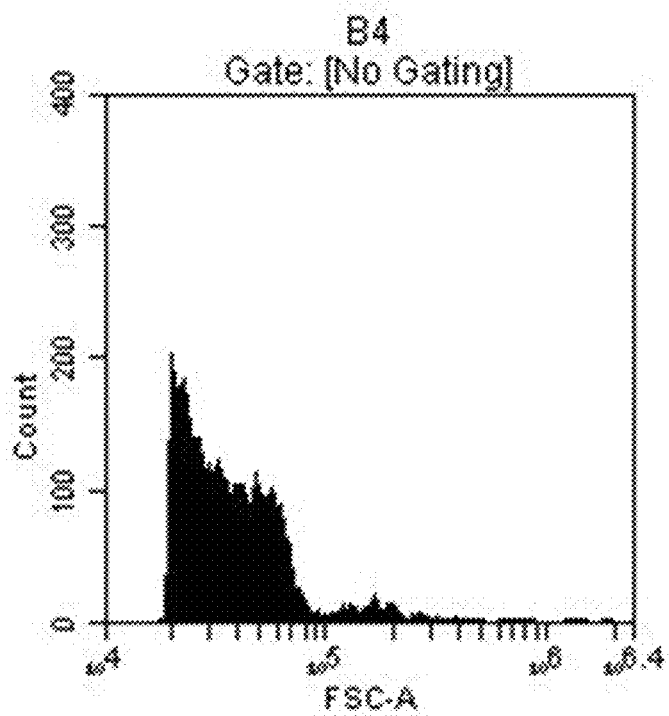
Figure 13A:
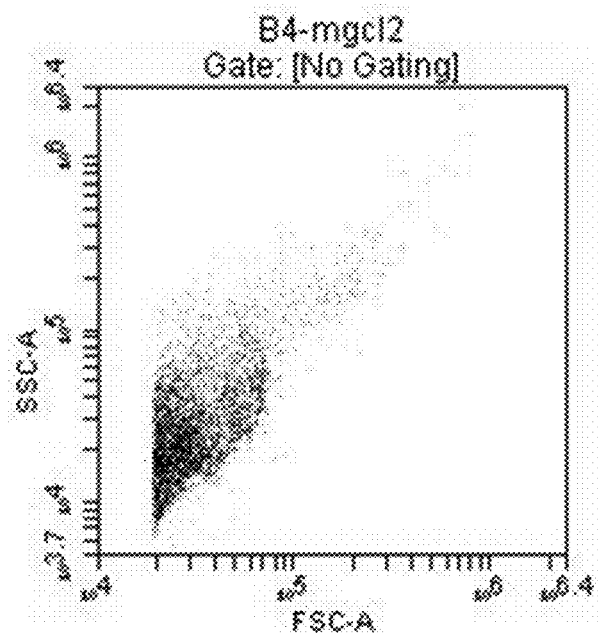
FIGS. 13A and 13B are scatter plots of flow cytometry data for a system containing 1 mM citrate buffer and 100 mM $MgCl_2$, pH 6.0.
Figure 13B:
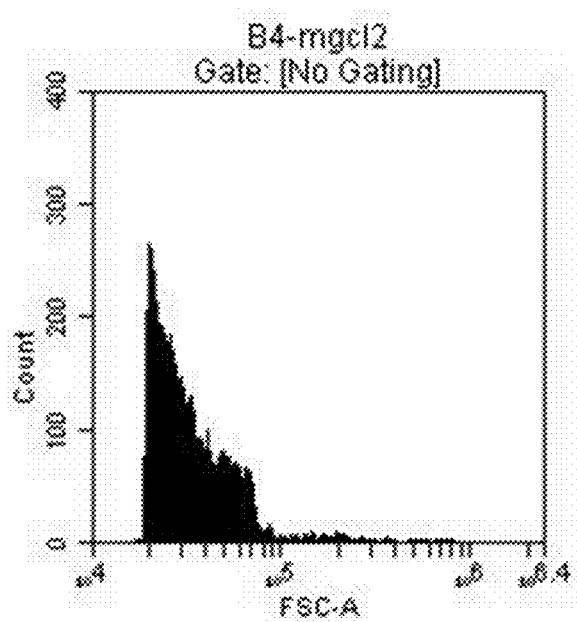

FIGS. 12A-12B show raw flow cytometry data scatter plots for the test sample containing the buffer alone, with no divalent cation-containing salt, LPS or DNA, and FIGS. 13A-13B show raw flow cytometry data scatter plots for the test sample containing the buffer along with 100 mM MgCl$_2$, with no LPS or DNA. FIGS. 12A and 13A show a flow cytometry side scattering to forward scattering intensity pattern that is characteristic of LC droplets having a bipolar configuration. Similarly, when the number of signal counts were plotted as a function of forward scattering intensity (FIGS. 12B and 13B), the droplets showed a range of scattering intensities that is characteristic of LC droplets having a bipolar configuration. This is the expected result, as no LPS is present to facilitate a shift of the LC droplets to the radial configuration.

Figure 14A:
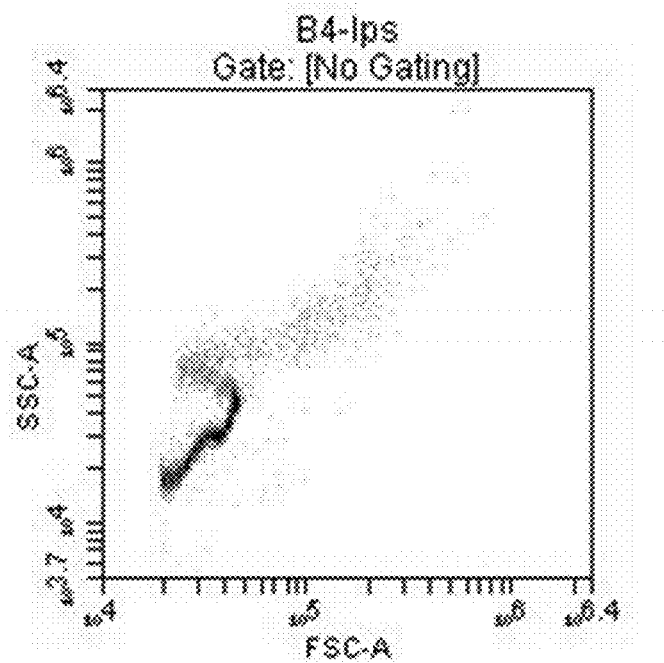
FIGS. 14A and 14B are scatter plots of flow cytometry data for a system containing 1 mM citrate buffer and 40 pg/mL LPS, pH 6.0.
Figure 14B:
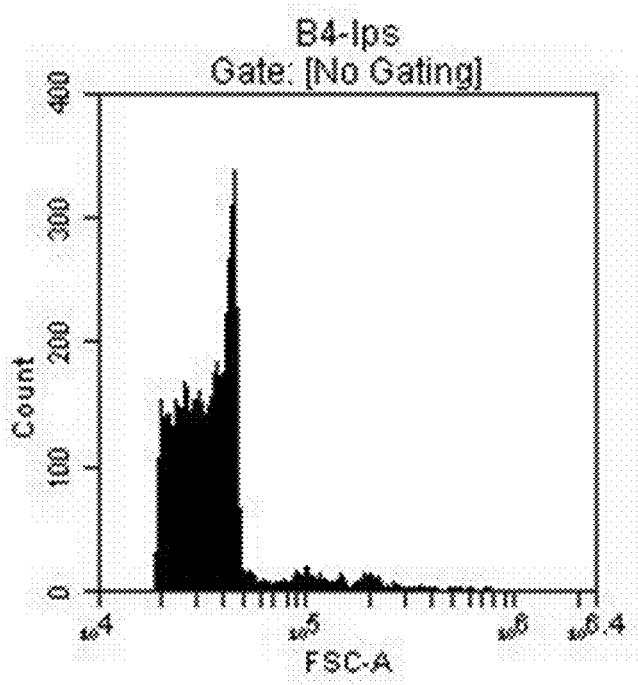

FIGS. 14A-14B show raw flow cytometry data scatter plots for the test sample containing the buffer along with 40 pg/mL LPS. In contrast to the results shown for the LPS-free test samples, FIG. 14A exhibits a 's-shaped' scatter plot with the narrower and downward-shifted distribution characteristic of droplets having the radial configuration. The narrowed range with a spiking forward scatter intensity shifted to a higher value that is seen in FIG. 14B is also characteristic of LC droplets exhibiting the radial configuration, a signal for the presence of LPS.

Figure 15A:
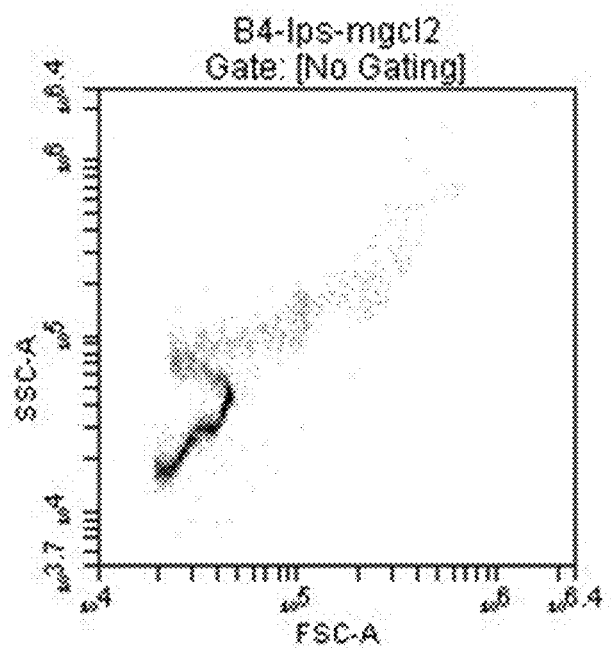
FIGS. 15A and 15B are scatter plots of flow cytometry data for a system containing 1 mM citrate buffer, 40 pg/mL LPS, and 100 mM $MgCl_2$, pH 6.0.
Figure 15B:
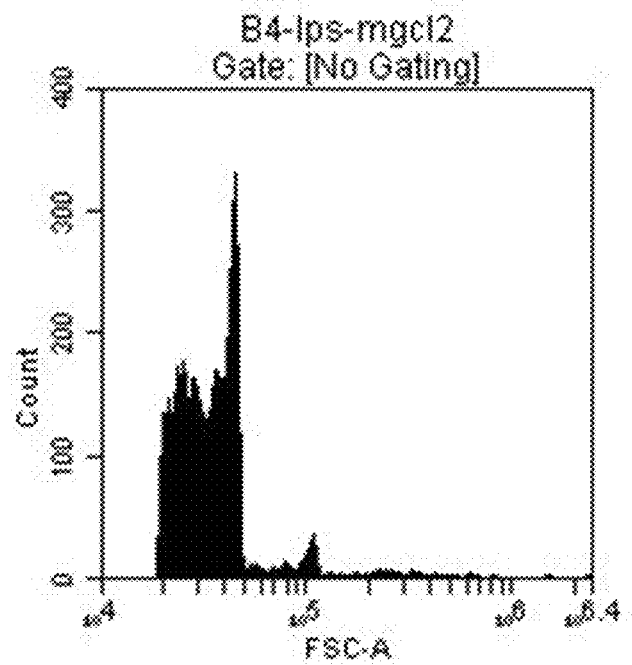
Figure 16A:
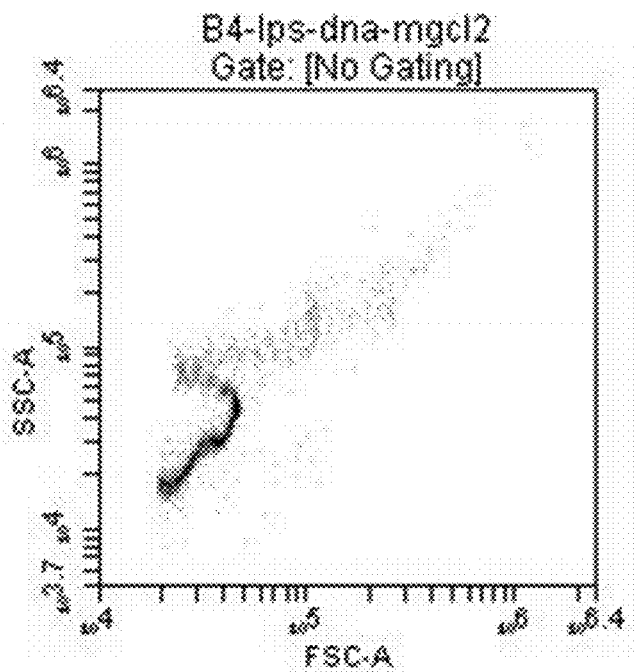
FIGS. 16A and 16B are scatter plots of flow cytometry data for a system containing 1 mM citrate buffer, 40 pg/mL LPS, 100 mM $MgCl_2$ and 100 mM $MgCl_2$, pH 6.0.
Figure 16B:
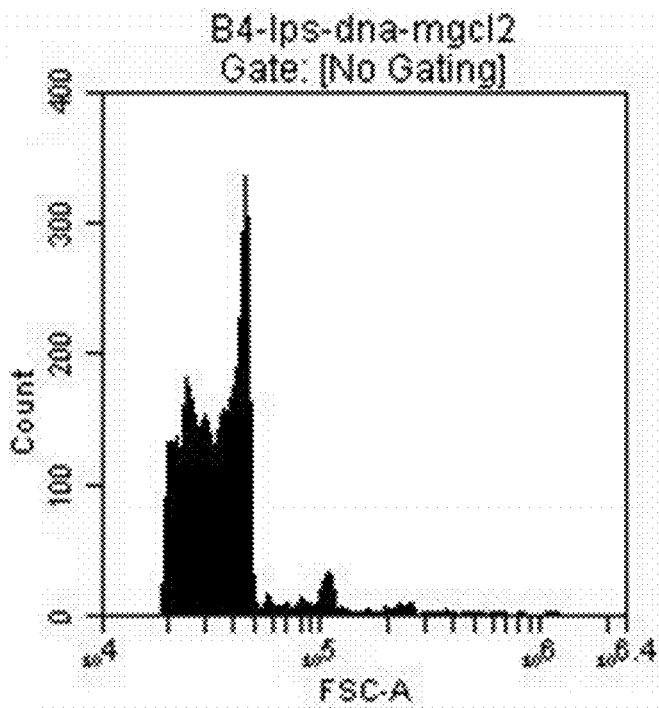

As further evidence that neither divalent cations nor DNA materially affect the results obtained using the LC droplet-based assay, FIGS. 15A-15B show raw flow cytometry data scatter plots for the test sample containing the buffer, 40 pg/mL LPS, and 100 mM MgCl$_2$. FIGS. 16A-16B show raw flow cytometry data scatter plots for the test sample containing the buffer, 40 pg/mL LPS, 100 mM MgCl$_2$, and 10 μg/mL DNA. Note that these scatter plots are substantially similar to those obtained for the LPS test sample that contained no divalent cation or DNA (FIGS. 14A and 14B).

Taken together, these results demonstrate that the LC droplet-based assay methods can be used with plasmid DNA samples in the presence of divalent salts used in their extraction. Furthermore, the LC droplet-based methods can used without loss of accuracy with any composition containing one or more divalent cations. This illustrates a further advantage of the LC droplet-based assay over the conventional LAL assay.

Those skilled in the art will recognize, or be able to ascertain using no more than routine experimentation, numerous equivalents to the specific materials and methods described herein. Such equivalents are considered to be within the scope of this invention and encompassed by the following claims.

We claim:

1. A liquid crystal-based system for detecting an analyte in a test sample, comprising: (a) a plurality of dispersed liquid crystal microdomains that are confined by an interface that generates one or more point defects in the liquid crystal microdomains, wherein the liquid crystal microdomains have a minor axis of between about 0.5 μm and about 200 μm, and wherein the liquid crystal microdomains are configured to change from a configuration having two point defects to a configuration having one point defect when contacted with an analyte; and (b) a test sample in contact with the liquid crystal microdomains that comprises a potential masking agent selected from the group consisting of a non-ionic surfactant, a chelating agent, a divalent cation, a protein, a nucleic acid, and combinations thereof.

2. The liquid crystal-based system of claim 1, further comprising a detector capable of characterizing the orientational order of the liquid crystal.

3. The liquid crystal-based system of claim 1, wherein at least one of the liquid crystal microdomains has one point defect.

4. The liquid crystal-based system of claim 1, wherein the test sample further comprises an analyte.

5. The liquid crystal-based system of claim 4, wherein the concentration of the analyte in the test sample is less than 1 μM.

6. The liquid crystal-based system of claim 4, wherein the analyte is endotoxin lipopolysaccharide (LPS) or the lipid A part of LPS.

7. The liquid crystal-based system of claim 1, wherein the potential masking agent is a non-ionic surfactant selected from the group consisting of Sorbitan monolaurate, Sorbitan monopalmitate, Sorbitan monostearate, Sorbitan monooleate, Sorbitan trioleate, Polyoxyethylene (20) sorbitan monolaurate, Polyoxyethylene (20) sorbitan monopalmitate, Polyoxyethylene (20) sorbitan monostearate, Polyoxyethylene (20) sorbitan mono-oleate, Polyoxyethylene (20) sorbitan tristearate, Polyoxyethylene (20) sorbitan tri-oleate, Triton X-100, Triton X-114, Triton X-405, Brij 30, Brij35, Brij 56, Brij 58, Brij78, Monolaurin, Nonoxynol-9, Pluronic P-123, Pluronic F-127, Cocamide DEA, and Cocamide MEA.

8. The liquid crystal-based system of claim 1, wherein the potential masking agent is a chelating agent is-selected from the group consisting of citric acid and salts thereof, ethylenediaminetetracaetic acid (EDTA) and salts thereof, aminotris(methylenephosphonic acid) (ATMP) and salts thereof, 1,2-bis(o-aminophenoxy)ethane-N,N,N',N'-tetraacetic acid (BAPTA) and salts thereof, bipyridines, diethylenetriamine (DETA), 1,4,7,10-tetraazacyclododecane-1,4,7,10-tetraacetic acid (DOTA) and salts thereof, diethylenetriaminepentaacetic acid (DTPA) and salts thereof, diethylenetriamine penta(methylene phosphonic acid) (DTMP) and salts thereof, ethylenediamine-N,N'-disuccinic acid (EDDS) and salts thereof, ethylenediamine tetra(methylene phosphonic acid) (EDTMP) and salts thereof, ethylene glycol-bis(β-aminoethyl ether)-N,N,N',N'-tetraacetic acid (EGTA) and salts thereof, 1-hydroxyethane 1,1-diphosphonic acid (HEDP) and salts thereof, gluconic acid and salts thereof, iminodiacetic acid (IDA) and salts thereof, nitrilotriacetic acid (NTA) and salts thereof, oxalic acid and salts thereof, polyaspartic acid (PASA) and salts thereof, and triethylenetetramine (TETA) and salts thereof.

9. The liquid crystal-based system of claim 1, wherein the potential masking agent is a divalent cation selected from the group consisting of $Mg^{2+}$, $Zn^{2+}$, $Ca^{2+}$, and $Cu^{2+}$.

10. The liquid crystal-based system of claim 1, wherein the potential making agent is DNA or RNA.

11. A method for detecting an analyte in a test sample comprising: (a) contacting one or more dispersed liquid crystal microdomains having one or more point defects with a test sample, wherein the liquid crystal microdomains are configured to change from a configuration having two point defects to a configuration having one point defect when contacted with an analyte, and wherein the test sample comprises a potential masking agent selected from the group consisting of a non-ionic surfactant, a chelating agent, a divalent cation, a protein, a nucleic acid, and combinations thereof; and (b) determining the configuration of the liquid crystal within the liquid crystal microdomains, wherein a change in the configuration of the liquid crystal within the liquid crystal microdomains after being contacted with the test sample from a configuration having two point defects to a configuration having one point defect indicates the presence of the analyte in the test sample.

12. The method of claim 11, wherein the change in the configuration of the liquid crystal within the liquid crystal microdomains is a change from bipolar to radial configuration.

13. The method of claim 11, wherein the test sample further comprises an analyte.

14. The method of claim 13, wherein the concentration of the analyte in the test sample is less than 1 µM.

15. The method of claim 13, wherein the analyte is endotoxin lipopolysaccharide (LPS) or the lipid A part of LPS.

16. A method for quantifying an analyte in a test sample comprising: (a) contacting a plurality of dispersed liquid crystal microdomains having one or more point defects with a test sample, wherein the liquid crystal microdomains are configured to change from a configuration having two point defects to a configuration having one point defect when contacted with an analyte, and wherein the test sample comprises a potential masking agent selected from the group consisting of a non-ionic surfactant, a chelating agent, a divalent cation, a protein, a nucleic acid, and combinations thereof, and (b) determining the configuration of the liquid crystal in the liquid crystal microdomains, wherein the percentage of liquid crystal microdomains exhibiting a particular the configuration having two point defects or the configuration having one point defect or set of configurations is correlated with the quantity of analyte in the test sample.

17. The method of claim 16, wherein the percentage of liquid crystal microdomains in the radial configuration is directly correlated with the quantity of analyte in the test sample.

18. The method of claim 16, wherein the test sample further comprises an analyte.

19. The method of claim 18, wherein the concentration of the analyte in the test sample is less than 1 µM.

20. The method of claim 18, wherein the analyte is endotoxin lipopolysaccharide (LPS) or the lipid A end of LPS.

* * * * *